(12) United States Patent
Skulachev et al.

(10) Patent No.: US 9,308,214 B2
(45) Date of Patent: Apr. 12, 2016

(54) METHOD FOR MODERATELY INCREASING THE PROTON CONDUCTIVITY OF BIOLOGICAL MEMBRANES WITH THE AID OF MITOCHONDRIA-TARGETED DELOCALIZED CATIONS

(75) Inventors: Vladimir P. Skulachev, Moscow (RU); Maxim V. Skulachev, Moscow (RU)

(73) Assignee: MITOTECH S.A., Luxembourg (LU)

( * ) Notice: Subject to any disclaimer, the term of this patent is extended or adjusted under 35 U.S.C. 154(b) by 801 days.

(21) Appl. No.: 13/128,966

(22) PCT Filed: Nov. 12, 2008

(86) PCT No.: PCT/RU2008/000706
§ 371 (c)(1),
(2), (4) Date: Jun. 1, 2011

(87) PCT Pub. No.: WO2010/056145
PCT Pub. Date: May 20, 2010

(65) Prior Publication Data
US 2011/0245207 A1    Oct. 6, 2011

(51) Int. Cl.
*A61K 31/66* (2006.01)
*A61K 31/352* (2006.01)

(52) U.S. Cl.
CPC .............. *A61K 31/66* (2013.01); *A61K 31/352* (2013.01)

(58) Field of Classification Search
CPC .............................. A61K 31/66; A61K 31/352
See application file for complete search history.

(56) References Cited

U.S. PATENT DOCUMENTS

| | | | |
|---|---|---|---|
| 5,538,974 A | 7/1996 | Ogawa et al. | |
| 6,331,532 B1 | 12/2001 | Murphy et al. | |
| 7,109,189 B2 | 9/2006 | Murphy et al. | |
| 2005/0065099 A1 | 3/2005 | Walkinshaw et al. | |
| 2007/0259908 A1 | 11/2007 | Fujii et al. | |
| 2007/0270381 A1 | 11/2007 | Murphy et al. | |
| 2008/0275005 A1 | 11/2008 | Murphy et al. | |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.

Clem et al. (2008) "Small-molecule inhibition of 6-phosphofructo-2-kinase activity suppresses glycolytic flux and tumor growth," Mol. Canc. Ther. 7(1):110-120.

Goldstein (2002) "Reactive oxygen species as essential components of ambient air," Biochemistry (Mosc.) 67:161-170.

Green (1974) "The electromechanochemical model for energy coupling in mitochondria," Biochimica et Biophysica Acta, 346:27-78.

Kirste et al. (1995) "Continuous-wave electron spin resonance studies of porphyrin and porphyrin-quinone triplet states," J. Chem. Soc. Perkin Trans. 2:2147-2152.

Murphy et al. (2007) Targeting antioxidants to mitochondria by conjugation to lipophilic cations. Annu. Rev. Pharmacol. Toxicol., 47:629-656.

Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.

Plotnikov et al. (2010) "New-generation Skulachev ions exhibiting nephroprotective and neuroprotective properties." Biochemistry (Mosc.), 75(2):145-150.

Skulachev et al. (2005) "Aging as mitochondria-mediated atavistic program. Can aging be switched off?" Ann. N.Y. Acad. Sci., 1057:145-164.

Skulachev et al. (2009) "An attempt to prevent senescence: a mitochondrial approach," Biochimica et Biophysica Acta., 1787:437-461.

Smith et al. (2008) "Mitochondria-targeted antioxidants in the treatment of disease,"Ann. N.Y. Acad. Sci., 1147:105-111.

Snow et al. (2010) "A double-blind, placebo-controlled study to assess the mitochondria-targeted antioxidant MitoQ as a disease-modifying therapy in Parkinson's disease," Mov. Disord. 25(11):1670-1674.

Stefanova et al. (2010) "Behavioral effects induced by mitochondria-targeted antioxidant SkQ1 in Wistar and senescence-accelerated OXYS rats," J. Alzheimer's Dis. 21:479-491.

Tauskela (2007) "MitoQ—a mitochondria-targeted antioxidant," IDrugs, 10:399-412.

Triet et al. (1993) "Anxiogenic stimuli in the elevated plus-maze," Pharmacol. Biochem. & Behav. 44:463-469.

(Continued)

*Primary Examiner* — Samira Jean-Louis
(74) *Attorney, Agent, or Firm* — Verrill Dana LLP; Wayne A. Keown

(57) ABSTRACT

The invention relates to biology and medicine, in particular, can be used in medicine for preparation of a pharmaceutical composition for specific, self-regulating uncoupling of mitochondria. The invention may be useful in treatment of diseases and conditions associated with violation of cellular metabolism, in treatment of obesity including its pathological forms, as well as in treatment of diseases associated with increased formation of free radicals and reactive oxygen species. In addition, the invention may be used in biotechnology for stimulation of growth of yeast and microorganisms as well as for stimulation of development of tissues and organs of plant and animal origin.

5 Claims, 9 Drawing Sheets

(56) References Cited

OTHER PUBLICATIONS

Antonenko, et al., "Protective effects of mitochondria-targeted antioxidant SkQ in aqueous and lipid membrane environments," J. Membr. Biol., 222:141-149 (2008).

Astrup, et al., "Low resting metabolic rate in subjects predisposed to obesity: a role for thyroid status 1-3," Am. J. Clin. Nutr. 63:879-883 (1996).

Berge, et al., "Pharmaceutical Salts," J. Pharma. Sci., 66(1):1-19 (1977).

Blaikie, et al., "Targeting Dinitrophenol to Mitochondria: Limitations to the Development of a Self-limiting Mitochondrial Protonophore," Biosci. Rep, 26:231-243 (2006).

Bray, et al., "Sibutramine produces dose-related weight loss," Obes. Res. 7(2):189-198 (1999).

Brand, et al. "The mechanism of the increase in mitochondrial proton permeability induced by thyroid hormones," Eur. J. Biochem. 206:775-781 (1992).

Byrom, "Nature of myxoedema," Clin. Sci. 1:273-285 (1933).

Clapham, et al., "Mice overexpressing human uncoupling protein-3 in skeletal muscle are hyperphagic and lean." Nature, 406:415-418 (2000).

Gong, et al., "Uncoupling protein-3 is a mediator of thermogenesis regulated by thyroid hormone, beta3-adrenergic agonists, and leptin," J. Biol. Chem., 272(39):24129-24132 (1997).

Green, et al., "Prevention of Mitochondrial Oxidative Damage as a Therapeutic Strategy in Diabetes," Diabetes, 53(1):S110-S118 (2004).

Hansford, et al., "Dependence of H2O2 formation by rat heart mitochondria on substrate availability and donor age," J. Bioenerg. Biomem. 29(1):89-95 (1997).

Hess, et al., "Biological and Chemical Applications of Fluorescence Correlation Spectroscopy: A Review," Biochem. 41(3):697-705 (2002).

Hvizdos, et al., "Orlistat: a review of its use in the management of obesity," Drugs, 58(4):743-760 (1999).

Li, et al., "Skeletal muscle respiratory uncoupling prevents diet-induced obesity and insulin resistance in mice," Nat. Med. 6(10):1115-1120 (2000).

Lou, et al., "Mitochondrial Uncouplers With an Extraordinary Dynamic Range," Biochem. J., 407:129-140 (2007).

Parascandola, "Dinitrophenol and bioenergetics: an historical perspective," Mol. Cell. Biochem., 5(1-2):69-77 (1974).

Poehlman, et al., "A review: exercise and its influence on resting energy metabolism in man," Med. Sci. Sports Exerc., 21(4):515-525 (1989).

Pozniakovsky, et al., "Role of mitochondria in the pheromone- and amiodarone-induced programmed death of yeast," J. Cell Biol., 168(2):257-69 (2005).

Skulachev, "A Biochemical Approach to the Problem of Aging: 'Megaproject' on Membrane-Penetrating Ions. The First Results and Prospects," Biochem. (Moscow), 72(12):1385-1396 (2007).

Starkov, et al., "6-ketocholestanol is a recoupler for mitochondria, chromatophores and cytochrome oxidase proteoliposomes," Biochim. Biophys. Acta. 1318:159-172 (1997).

Weyer, et al., "Development of beta3-adrenoceptor agonists for the treatment of obesity and diabetes—an update," Diabetes Metab., 25:11-21 (1999).

Zettl, et al., "Investigation of micelle formation by fluorescence correlation spectroscopy," J. Phys. Chem. B. 109:13397-13401 (2005).

International Search Report, PCT/RU2008/000706, Aug. 13, 2009 (3 pages).

PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).

International Search Report and Written Opinion of the International Searching Authority, PCT/US12/40711, Aug. 20, 2012 (9 pages).

Adlam et al. (2005) "Targeting an antioxidant to mitochondria decreases cardiac ischemia-reperfusion injury," FASEB J., 19:1088-1095.

Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73(12):1300-1316 (+ 3 fig. pages).

Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.

Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.

Becker (2004) "New concepts in reactive oxygen species and cardiovascular reperfusion physiology" Cardiovascular Research, 61:461-470.

Kasahara et al. (2005) "Manganese Superoxide Dismutase protects against oxidation-induced apoptosis in mouse retinal pigment epithelium: implications for age-related macular degeneration," Invest. Ophthalmol. Vis. Sci., 46(9):3426-3434.

Havens et al. (2006) "Regulation of Late G1/S Phase Transition and APCCdh1 by Reactive Oxygen Species," Mol. & Cell. Biol., 26(12):4701-4711.

Holloszy (1998) "Longevity of exercising male rats: effect of an antioxidant supplemented diet," Mechanisms of Ageing and Development, 100:211-219.

King et al. (2004) "Mitochondria-derived reactive oxygen species mediate blue light-induced death of retinal pigment epithelial cells," Photochem. and Photobiol., 79(5):470-475.

Doughan et al. (2007) "Original Research Communication: Mitochondrial Redox Cycling of Mitoquinone Leads to superoxide Production and Cellular Apoptosis," Antioxid. & Redox Signal., 9(11):1825-1836.

Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.

Longo et al. (2005) "Programmed and altruistic ageing," Nature Reviews Genetics, 6:866-872.

Kirschner et al. (1994) "Role of iron and oxygen-derived free radicals in ischemia-reperfusion injury" J. Am. Coll. Surg., 179:103-117.

Popova et al. (2010) "Scavenging of Reactive Oxygen Species in Mitochondria Induces Myofibroblast Differentiation," Antiox. & Redox. Signal., 13(9):1297-1307.

Popova et al. (2006) "MitoQ induced miofibroblast differentiation of human fibroblasts," Biochimica et Biophysica Acta, S:433-434.

Reliene et al. (2007) "Antioxidants suppress lymphoma and increase longevity in atm-deficient mice," J. Nutrition, 137:229S-232S.

Reddy (2006) "Mitochondrial oxidative damage in aging and Alzheimer's disease: implications for mitochondrially targeted antioxidant therapeutics," J. Biomedicine and Biotech., Art.ID 31372:1-13.

Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.

Skulachev (2005) "Critical Review: How to Clean the Dirtiest Place in the Cell: Cationic Antioxidants as Intramitochondrial ROS Scavengers," IUBMB Life, 57(4/5):305-310.

Tompkins et al. (2006) "Mitochondrial dysfunction in cardiac ischemia-reperfusion injury: ROS from complex I, without inhibition," Biochim Biophys. Acta. 1762:223-231.

Sidorova et al. (2004) "Transcriptional activation of cytochrome P450 1A1 with alpha-tocopherol," Bull Exp. Bio. Med., 138(3):233-236.

Mecocci et al. (2000) "Plasma antioxidants and longevity: a study on healthy centenarians," Free Radical Biology and Medicine, 28(8):1243-1248.

Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73(12):1317-1328.

(56) References Cited

OTHER PUBLICATIONS

Orr et al. (2003) "Effects of overexpression of copper—zinc and manganese superoxide dismutases, catalase, and thioredoxin reductase genes on longevity in *Drosophila melanogaster*," J. Biol. Chem., 278(29):26418-26422.

Papp et al. (1999) "Glutathione status in retinopathy of prematurity," Free Radic. Biol. & Med., 27(7-8):738-743.

Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.

Sheu et al. (2006) "Targeting antioxidants to mitochondria: a new therapeutic direction," Biochimica et Biophysica Acta, 1762:256-265.

Yildirim et al. (2005) "Role of oxidative stress enzymes in open-angle glaucoma," Eye, 19:580-583.

Zweier et al. (1987) "Direct measurement of free radical generation following reperfusion of ischemic myocardium," PNAS USA, 84:1404-1407.

Riess et al. (2004) "Reduced reactive O2 species formation and preserved mitochondrial NADH and [Ca2+] levels during short-term 17° C. ischemia in intact hearts," Cardiovascular Research, 61:580-590.

Sundaresan et al. (1995) "Requirement for Generation of H2O2 for Platelet-Derived Growth Factor Signal Transduction," Science, 270:296-299.

International Search Report and Written Opinion of the International Searching Authority, PCT/RU2007/000044, Nov. 1, 2007 (9 Pages).

International Search Report dated Dec. 20, 2007 and International Preliminary Report on Patentability dated Nov. 10, 2009, PCT/RU2007/000171 (16 pages).

International Search Report and Written Opinion of the International Searching Authority, PCT/RU2007/000355, Mar. 27, 2008 (10 pages).

PCT International Preliminary Report on Patentability for International Application No. PCT/RU2007/000043, issued Aug. 4, 2009 (7 pages).

PCT International Search Report for PCT Application No. PCT/RU2007/000043, mailed Nov. 1, 2007, 2 pages.

PCT International Search Report and Written Opinion of the International Searching Authority for PCT Application No. PCT/RU2006/000546, mailed Jul. 5, 2007, 14 pages.

International Search Report and Written Opinion of the International Searching Authority, PCT/RU2009/000295, Feb. 25, 2010, 7 pages.

International Search Report and Written Opinion, PCT/RU2009/000621, dated Aug. 12, 2010 (12 pages).

International Search Report and Written Opinion, PCT/RU2006/000394, dated Nov. 2, 2006 (6 pages).

International Search Report and Written Opinion, PCT/RU2006/000547, dated Jul. 5, 2007 (7 pages).

Severin et al., "Penetrating Cation/Fatty Acid Anion Pair as a Mitochondria-Targeted Protonophore", www.pnas.org/cgi/doi.10.1073/pnas.0910216107 (2009).

METHOD FOR MODERATELY INCREASING THE PROTON CONDUCTIVITY OF BIOLOGICAL MEMBRANES WITH THE AID OF MITOCHONDRIA-TARGETED DELOCALIZED CATIONS

CROSS-REFERENCE TO RELATED APPLICATION

This application claims the benefit of PCT/RU2008/000706, entitled "Method for Moderately Increasing the Proton Conductivity of Biological Membranes With the Aid of Mitochondria-Targeted Delocalized Cations," filed on Nov. 12, 2008. The entirety of the aforementioned application is herein incorporated by reference.

FIELD OF THE INVENTION

The invention relates to pharmacology, medicine, in particular to a class of mitochondria-targeted compounds which can be used in pharmaceutical compositions of medicines (preparations) for prophylaxis and treatment of various diseases and pathological states in which it is useful to moderately increase proton permeability of membranes that leads in particular to a moderate decrease in the inner mitochondrial membrane potential that in turn may lead to a variety of favorable effects on an organism.

BACKGROUND

Mitochondria are found in all eukaryotic cells and are involved in a wide variety of processes necessary to cell life including ATP production, control over reduction level of cellular components, calcium homeostasis, biosynthesis of metabolites etc. In addition, mitochondria are the major source of reactive oxygen species (ROS) in a cell and play an important role in the mechanism of programmed cell death.

Normally, the main function of mitochondria is energy production stored in an ATP molecule which is then used by a cell for different needs. The energy is stored in ATP by a process called oxidative phosphorylation. The essence of oxidative phosphorylation is to transfer electrons from NADH through the mitochondrial electron transport chain to oxygen that leads to formation of a water molecule and creation of the electrochemical proton gradient that is further used to synthesize an ATP molecule. In warm-blooded animals, part of the energy stored in the electrochemical proton gradient is used to maintain a constant body temperature and is not coupled to the ATP synthesis. The uncoupling of oxidative phosphorylation from ATP synthesis occurs due to free fatty acids located in the cytoplasm of a cell. The uncoupling mechanism is as follows: at the outer surface of mitochondrial membrane, a fatty acid anion (RCOO$^-$) binds an H$^+$ ion pumped from the mitochondrial matrix by the respiratory chain enzymes. The resulting protonated form of the fatty acid (RCOOH) crosses the membrane and dissociates at its inner surface yielding RCOO$^-$ and H$^+$. The latter compensates for the lack of H$^+$ ions inside mitochondria removed from the mitochondrial matrix by the respiratory chain. The resulting RCOO$^-$ anion returns to the outside by means of mitochondrial proteins—anion transporters, in particular, the ATP/ADP-antiporter or special uncoupling proteins called UCP (uncoupling protein). Normally, 20-25% of the total metabolism of warm-blooded animals is directed at maintaining a constant body temperature, and the mechanism of heat production is associated with the uncoupling of respiration from ATP synthesis at the expense of an increase in the proton permeability. The increase in proton permeability or "mild uncoupling" can be used both for thermogenesis and for body weight control, for stimulation of carbohydrate metabolism, as well as to control the level of ROS generation by mitochondria. Mitochondrial malfunction, in particular, malfunction of mechanisms of mild uncoupling can be expressed in the development of various pathologies, especially obesity, diabetes, as well as pathologies associated with the development of oxidative stress: ischemic tissue damage, Parkinson's disease, Alzheimer's disease, premature aging.

One of the most acute problems of modern health care is a constant increase in the number of overweight people. According to recent estimates by the World Health Organization (WHO), in 2005 worldwide approximately 1.6 billion adults (aged >15 years) were overweight and at least 400 million adults were obese. According to WHO estimates, by 2015, approximately 2.3 billion adults will be overweight and more than 700 million adults will be obese. Obesity results from violation of the energy balance between energy supply and energy loss that causes storage of excess energy as fat. Currently, obesity is an acute problem in many countries. Worldwide, the number of people who are overweight and suffering from morbid obesity is increasing every year (Koplman (2000) *Nature*, 404: 635-643.). Overweight increases the risk for many serious medical conditions, such as non-insulin-dependent diabetes (type 2 diabetes), ischemic heart disease, hypertension and stroke, gallbladder disease, some cancers (endometrial, ovarian, breast, prostate, colon and rectum, gallbladder, pancreas, liver and kidneys), as well as psycho-social problems.

A variety of diets promote effective weight loss, however, more than 90% of the people, who lose weight through diet, further fully return former weight. For people who can not control weight through diet and exercise and are suffering from diseases associated with obesity, pharmacological treatment may be effective.

Any obesity treatment is aimed at reducing energy supply, increasing energy loss, or a combination of these two approaches is used. Currently, the former approach aimed at reducing energy supply, i.e. food, is mainly used for obesity treatment. The effect is achieved by medical therapy that suppresses the activity of saturation points in the brain (sibutramine, see, e.g., Bray, et al. (1999) *Obes. Res.* 7:189-198), or reduces the efficiency of absorption of food in the gastrointestinal tract (e.g., Hvizdos, et al. (1999) *Drugs,* 58:743-760). It was shown that some compounds can not only decrease energy supply but stimulate metabolism, i.e., increase energy loss. Nevertheless, the safest and most effective method of weight loss is exercise. In this case, the effect is achieved due to stimulation of metabolism by exercise and, as a consequence, an increase in energy loss (Poehlman, et al. (1989). *Med. Sci. Sports Exerc.,* 21:515-525). The same effect can be achieved with compounds that stimulate metabolism by uncoupling of mitochondria, i.e., by reducing the efficiency of energy supply and thus increasing energy loss. The effectiveness of this approach has been repeatedly confirmed by clinical data on the use of well-known uncoupler 2,4-dinitrophenol (DNP) (Parascandola, et al. (1974) *Mol. Cell. Biochem.* 5:69-77) or thyroid hormones stimulating metabolism (Astrup, et al. (1996) *Am. J. Clin. Nutr.* 63:879-883), as well as with animals using β3-adrenoceptor agonists (Weyer, et al. (1999) *Diabetes Metab.* 25:11-21), or by expressing uncoupling protein UCP3 (uncoupling protein 3) (Clapham, et al. (2000) *Nature,* 406:415-418). The experiments showed the effectiveness of the approach but revealed significant weaknesses which prevent the use of uncouplers in clinical practice, namely:

1) Protonophores or uncouplers which facilitate the movement of protons across the inner mitochondrial membrane were used in clinical practice in 30-ies of the 20 century. These molecules are often weak lipophilic acids (e.g., 2,4-dinitrophenol (DNP)), and the protonated form of such acids can freely penetrate via the inner mitochondrial membrane into the matrix where deprotonation of the molecule occurs, whereupon a negatively charged anion is ejected from the mitochondrial matrix and can be reprotonated with the repetition of the cycle.

Many clinical trials demonstrated the effectiveness of DNP against obesity. By 1934, more than 100,000 patients were treated with DNP. By the end of the treatment, almost all of the patients lost weight with varying degrees of efficiency but the favorable signs were accompanied by severe side effects. Overdose caused muscle weakness, high fever in a patient, that in some cases led to death. In addition, in many patients, prolonged use of the preparation led to the development of cataract and vision loss. In 1938, all of these facts led to the strict ban on the use of this preparation for the treatment of any disease. However, the fact that the treatment with DNP actually led to weight loss in patients indicates the fidelity of the approach.

2) Treatment of obesity with thyroid hormones normally regulating body metabolism has a long history (Byrom, et al. (1933) *Clin. Sci.*, 1:273-285). It was shown that stimulation of energy metabolism by thyroid hormones occurs due to uncoupling of mitochondria. The mechanism of uncoupling induced by thyroid hormones is still not entirely clear. To date, there are two theories and each has a number of conclusive evidence. The first theory implies that thyroid hormones interact directly with the mitochondrial membrane changing its physicochemical properties, that leads to an increase in proton permeability and uncoupling of mitochondria. In addition, thyroid hormones can cause changes in phospholipid composition of mitochondrial membrane not directly but through a change in the level of transcription of a number of proteins involved in lipid metabolism (Brand, et al. (1992) *Eur. J. Biochem.*, 206:775-78). In each of these cases, uncoupling of mitochondria and stimulation of metabolism occur. According to the second theory, hormones can alter the level of transcription of proteins directly involved in the regulation of mitochondrial membrane coupling, in particular, of the proteins of the UCP family (Gong, et al. (1997) *J. Biol. Chem.*, 272:24129-24132).

Over the long history of the use of thyroid hormones for the treatment of obesity it has been shown that despite high efficacy of therapy, thyroid hormones, even at low concentrations, can cause numerous side effects, such as tachycardia, increased heart weight, thyroid atrophy, muscle mass loss etc. (Klein, et al. (1984) *Am. J. Med.*, 76:167-172; Mittleman, et al. (1984) *South. Med. J.*, 77:268-270). A large number of side effects led to the fact that currently thyroid hormones are not used in clinical practice for treating obesity.

3) The development of specific $\beta_3$-adrenergic receptor agonist which regulates the activity of uncoupling protein UCP1 in brown fat was a great achievement of pharmacology. The high specificity of the compound leads to its low toxicity and virtually complete absence of side effects. Numerous experiments on animals showed that the $\beta_3$-adrenergic receptor agonist increases insulin sensitivity in diabetic animals and stimulates weight loss in animals due to specific reduction of adipose tissue. However, human clinical trials showed that this compound is absolutely not effective. The most likely explanation for this observation is that there is almost no brown fat in adults whereas in rodents which were used in most of the experiments, the amount of brown fat declines insignificantly with age.

4) It was shown that induction of expression of uncoupling protein UCP1 or UCP3 leads to specific uncoupling of muscle mitochondria and prevents obesity and development of diabetes in mice fed a high-calorie diet (Li, et al. (2000) *Nat. Med.*, 6:1115-1120). However, this approach cannot be applied to humans since any form of manipulation of the human genome is currently prohibited even if the complexity of method for increasing protein expression is not taken into account.

Thus, at present, development of nontoxic pharmaceuticals that enhance proton permeability of the mitochondrial membrane is promising. Self-regulating preparations that can selectively increase proton permeability of mitochondria with high membrane potential seem to be most promising. Required specificity can be provided by uncoupler whose concentration in mitochondria depends on their membrane potential. Such approach was already used earlier (Blaikie, et al. (2006) *Biosci. Rep.* 26:231-243). The authors synthesized a compound based on penetrating cation tetraphenylphosphonium bound to a molecule of 2,4-dinitrophenol. This molecule did accumulate in mitochondria depending on membrane potential but did not reveal its protonophore properties and could not be used for uncoupling of mitochondria.

Apart from stimulation of metabolism to combat obesity, the use of preparations that cause mild uncoupling may have an antioxidant effect. It was shown that in the respiratory chain there are two main sites where generation of ROS is possible; those sites are complex I (generation of superoxide into the mitochondrial matrix) and complex III (generation of superoxide into the mitochondrial matrix and the mitochondrial intermembrane space). Contribution of each of these complexes into the overall level of generation of ROS is still not clear, however, it was shown that the maximum ROS generation can be observed in complex I due to reverse electron transfer from complex II to complex I. This phenomenon can be observed under conditions when mitochondria are maximally coupled, membrane potential reaches a maximum and ATP consumption in cells decreased. The electrons of complex II acquire the ability to move against main flow of electrons, thus wasting membrane potential energy. In addition, under conditions of high membrane potential and low ATP consumption, inhibition of mitochondrial respiration and reduction of all parts of the respiratory chain occur. In that case, leakage of electrons to oxygen to form superoxide can also occur in complex III. The entire system is heavily dependent on the value of membrane potential, for example, decrease in membrane potential by only 10 mV (about 5%) leads to decrease in ROS generation by 70% (Hansford et al). Thus, to achieve a powerful antioxidant effect of compounds, even mild uncoupling, at which there are no significant violations of mitochondrial function yet, is sufficient.

SUMMARY

The present disclosure provides compounds of structure (I)

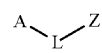

wherein: "A" is a hydrogen, substituted or unsubstituted alkyl, aryl, heteroaryl, cycloalkyl or heterocyclic group, or is a substituted or unsubstituted aromatic, saturated, or partially unsaturated polycyclic system: "L" is a linker group comprising a substituted or unsubstituted hydrocarbon chain with a length of up to 20 carbon atoms, optionally containing double- or triple-bonds, heteroatoms, such as —S—, —N—, and optionally having inclusions of groups —C(O)O—, —C(O)—, —C(O)N(H)—; and "Z" is a positively-charged targeting group, and solvates, salts, isomers, and prodrugs thereof.

In some embodiments, the compound increases proton permeability of biological membranes, has protonophore activity, or reduces mitochondrial membrane potential.

In some embodiments, the compound forms a complex with a fatty acid anion, and in some embodiments the compound/fatty acid anion complex passes through mitochondrial membranes, or passes from the inner mitochondrial membrane to the intermembrane space.

In certain embodiments of the compound, Z is a lipophilic cation which is triphenylphosphonium, triphenylammonium, or tributylammonium, or Z is rhodamine, berberine, or palmatine, or derivatives thereof.

The disclosure also provides a method for reducing the amount of free radicals and reactive oxygen species in a cell, comprising contacting the cell with the compound (I) of claim 1.

Another aspect of the disclosure is a method for stimulating cell metabolism or increasing viability and/or productivity of cells producing, comprising contacting a cell with the compound (I) of claim 1. In some embodiments, the cell is a human cell, a mammalian cell, a plant cell, or a fungal cell, a cell in culture, a protoplast, a cell in an organism, a normal cell, a cancer cell, and/or a stem cell.

In some embodiments, the cell is a plant cell, a plant cell in culture, is part of a plant at any stage of the plant's development, and includes genetically modified plants, is a fungal cell and/or in a culture of fungal cells; including to increase viability and/or productivity of cells producing pharmacologically applicable protein and peptides, such as antibodies.

Yet another aspect is a method of increasing proton permeability of a biological membrane in a cell, comprising contacting the cell with the compound (I). In some embodiments, the biological membrane is a mitochondrial membrane within the cell, In another aspect, the disclosure provides a pharmaceutical composition comprising a therapeutically effective amount of the compound (I) and a pharmaceutically acceptable carrier.

Methods of treating obesity or diabetes in a subject are also provided, comprising administering a therapeutic amount of the present pharmaceutical composition of claim 18 to an obese or diabetic subject, respectively.

Another aspect of the disclosure is a method of protecting healthy cells in a patient from free radical damage during chemotherapy, radiotherapy, or photodynamic therapy, comprising administering to the patient a therapeutic amount of the pharmaceutical composition of claim 18 before the patient receives chemotherapy, radiotherapy, or photodynamic therapy. The disclosure also provides a method of using a pharmaceutical composition for treatment of a disease in which a decrease in the amount of free radicals and reactive oxygen species in an organism is therapeutic.

The pharmaceutical composition of the disclosure can also be used in cosmetic procedures, healing of surgical sutures, preventing damage to a healthy tissue during surgery, healing or preventing burn tissue lesions, against inflammation, for conservation of graft material, to combat rejection of transplanted tissues and organs, to increase in lifespan of an organism, the fight against aging, and in combination with hormone therapy, such as in combination with epiphysis hormones, and thyroid hormones, including dihydroepiandrosterone or melatonin.

BRIEF DESCRIPTION OF DRAWINGS

The foregoing and other objects of the present disclosure, the various features thereof, as well as the invention itself may be more fully understood from the following description, when read together with the accompanying drawings.

DESCRIPTION

Figure 1:
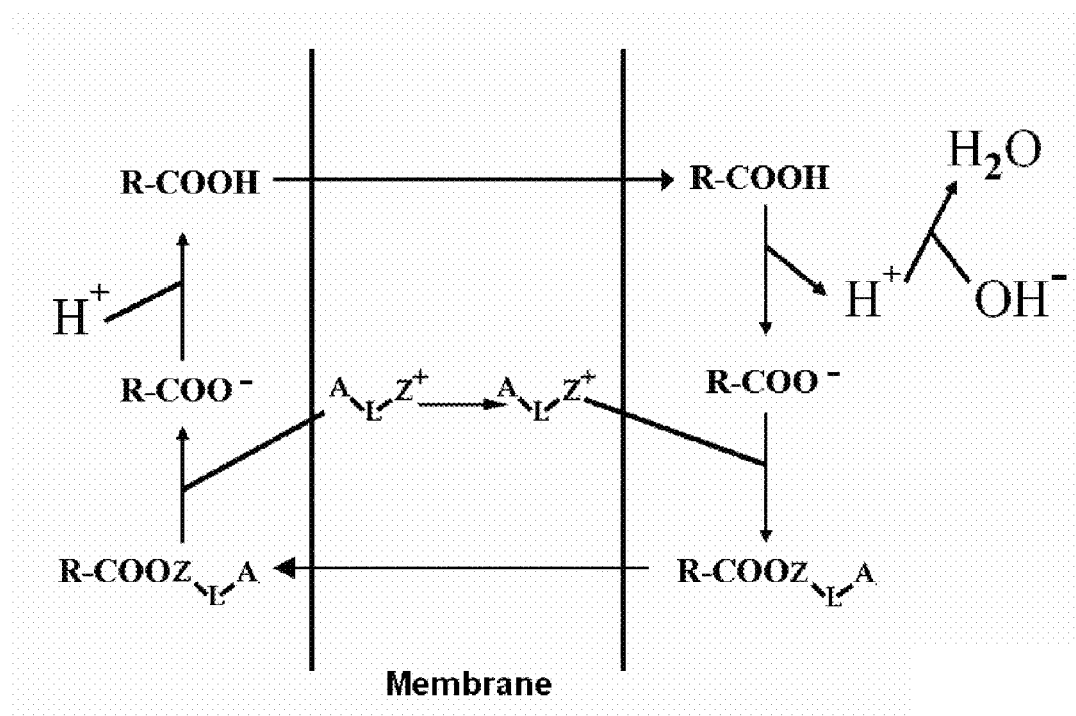
FIG. 1 is a schematic representation of the induction of proton permeability by fatty acids in the presence of mitochondria-targeted protonophores of the disclosure.

Throughout the text of a description of the invention various documents are cited. Each document cited here (including all patents, patent applications, scientific publications, specifications and manufacturer's instructions etc.), above or below, is introduced in full in this invention by reference.

Prior to the detailed description of the invention follows, one should understand that the invention is not limited to the particular methodology, protocols, and reagents described here, as they are subject to change. In addition, it should be understood that in the present invention, the terminology is used to describe particular embodiments only and does not limit the scope of the present invention which will be limited only by the appended claims. Unless otherwise specified, all technical and scientific terms used here have the same meanings that are understandable to those skilled in the art.

DEFINITIONS

A "protonophore" is a compound capable of electrogenic transport of protons across the inner mitochondrial membrane that leads to the fall in membrane potential and uncoupling of oxidation from phosphorylation. A "mitochondria-targeted protonophore" is a compound that targetedly accumulates in mitochondria and increases proton permeability of the inner mitochondrial membrane (i.e., decreases proton electrochemical potential of this membrane).

An "uncoupler" is a compound that causes uncoupling of respiration from oxidative phosphorylation in mitochondria. The mechanism of uncoupling is associated with a decrease in mitochondrial membrane potential due to protonophore activity of compounds or induction of endogenous proton permeability of membranes. A "Self-regulating uncoupler" is a compound whose uncoupling ability depends on the value of mitochondrial membrane potential. "Mild uncoupling or moderate uncoupling" is a reversible decrease in mitochondrial membrane potential that does not cause the suppression of respiration, respiratory chain component damage or violation of physicochemical properties of mitochondrial membranes.

The term "substituted or unsubstituted alkyl group" refers to substituted or unsubstituted saturated or unsaturated linear, branched or cyclic carbon chain. Preferably, this this chain contains from 1 to 10 carbon atoms, i.e., 1, 2, 3, 4, 5, 6, 7, 8, 9 or 10, for example, methyl, ethyl methyl, ethyl, propyl, iso-propyl, butyl, iso-butyl, tert-butyl, pentyl, hexyl, heptyl, octyl. In addition, the term "substituted or unsubstituted alkyl group" in the present invention also includes heteroalkyl group which is saturated or unsaturated linear or branched carbon chain. Preferably, this chain contains from 1 to 9 carbon atoms, i.e., 1, 2, 3, 4, 5, 6, 7, 8, 9, for example, methyl, ethyl, propyl, iso-propyl, butyl, iso-butyl, sec-butyl, tert-butyl, pentyl, hexyl, heptyl, octyl, which is interrupted once or several times, e.g., 1, 2, 3, 4, 5 times, by same or different heteroatoms. Preferably, heteroatoms are selected from O, S, and N, for example, $CH_2-O-CH_3$, $CH_2-O-C_2H_5$, $C_2H_4-O-CH_3$, $C_2H_4-O-C_2H_5$ etc.

The term "substituted or unsubstituted aryl group" preferably refers to aromatic monocyclic ring containing 6 carbon atoms, aromatic bicyclic ringed system containing 10 carbon atoms or aromatic ringed tricyclic system containing 14 carbon atoms. Examples are phenyl, naphthalenyl or anthracenyl. In addition, the term "substituted or unsubstituted aryl group" in the present invention also includes substituted or unsubstituted aralkyl group. The term "substituted or unsubstituted aralkyl group" refers to alkyl moiety which is substituted by aryl, and alkyl and aryl are as defined above. An example is benzene radical. Preferably, in this context, alkyl chain may contain from 1 to 8 carbon atoms, i.e., 1, 2, 3, 4, 5, 6, 7 or 8, for example, methyl, ethyl, propyl, iso-propyl, butyl, iso-butyl, sec-butenyl, tert-butyl, pentyl, hexyl, heptyl, octyl. Aralkyl group is optionally substituted at alkyl and/or aryl moiety. Preferably, the aryl may be attached to alkyl group is phenyl, naphthalenyl or anthracenyl.

The terms "substituted or unsubstituted heterocyclic group," alone or in combination with other terms, represent, unless otherwise stated, cyclic versions of "alkyl" and "heteroalkyl" groups, respectively, preferably, with 3, 4, 5, 6, 7, 8, 9 or 10 atoms forming ring, for example, cyclopropyl, cyclobutyl, cyclopentyl, cyclohexyl, cycloheptyl, cyclooctyl etc. It is implied that the terms "cycloalkyl" and "heterocycloalkyl" also include their bicyclic, tricyclic and polycyclic versions. If bicyclic, tricyclic or polycyclic rings are formed, it is preferable that corresponding rings are linked together by two adjacent carbon atoms, but as an alternative, two rings may be linked via the same carbon atom, i.e., they form spiro ring system or they form "bridged" ring systems. The term "substituted or unsubstituted heterocyclic group" preferably refers to saturated ring having five atoms, of which at least one is N, O or S atom, and which optionally contains one additional O atom or one additional N atom; saturated ring having six atoms, of which at least one is N, O or S atom, and which optionally contains one additional O atom or one additional N atom or two additional N atoms; or saturated bicyclic ring having nine or ten atoms, of which at least one is N, O or S atom, and which optionally contains one, two or three additional N atoms. "Cycloalkyl" and "heterocycloalkyl" groups are optionally substituted. Additionally for heterocycloalkyl, heteroatom may be in a position at which heterocycle is linked to the rest of the molecule. Preferred examples of cycloalkyl include cyclopropyl, cyclobutyl, cyclopentyl, cyclohexyl, 1-cyclohexenyl, 3-cyclohexenyl, cycloheptyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[2.2.1]heptyl, bicyclo[2.2.2]octyl, adamantyl and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, 1,8-diazaspiro-[4,5]decyl, 1,7-diazaspiro[4,5]decyl, 1,6-diazaspiro[4,5]decyl, 2,8-diazaspiro[4,5]decyl, 2,7-diazaspiro[4,5]decyl, 2,6-diazaspiro[4,5]decyl, 1,8-diazaspiro[5,4]decyl, 1,7-diazaspiro[5,4]decyl, 2,8-diazaspiro[5,4]decyl, 2,7-diazaspiro[5,4]decyl, 3,8-diazaspiro[5,4]decyl, 3,7-diazaspiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, 2-piperazinyl, and the like.

The term "polycyclic system" refers to bicyclic, tricyclic or polycyclic cycloalkyl or heterocycloalkyl variant comprising at least one double and/or triple bond. Nevertheless, alicyclic system is not aromatic or heteroaromatic, i.e., there is no system of conjugated double bonds or free electron pairs. Thus, the maximum number of double and/or triple bonds in alicyclic system is determined by the number of atoms in ring, for example, in cyclic system having up to 5 atoms, alicyclic system contains one double bond, in cyclic system having 6 atoms, alicyclic system contains up to two double bonds. Thus, defined below, the term "cycloalkenyl" is a preferred embodiment of alicyclic ring system. Alicyclic systems are optionally substituted.

The term "substituted or unsubstituted heteroaryl group" preferably refers to five- or six-membered aromatic monocyclic ring, wherein at least one of carbon atoms is replaced by 1, 2 or 3 (for five-membered ring) or 1, 2, 3, or 4 (for six-membered ring) same or different heteroatoms, for example, preferably selected from O, N and S; aromatic bicyclic ring system in which 1, 2, 3, 4, 5 or 6 carbon atoms of 8, 9, 10, 11 or 12 carbon atoms are replaced by identical or different heteroatoms, for example, preferably selected from O, N and S; or tricyclic aromatic ring system in which 1, 2, 3, 4, 5 or 6 carbon atoms of 13, 14, 15 or 16 carbon atoms are replaced by same or different heteroatoms, preferably selected from O, N and S. Examples include furanyl, thiophenyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl. In addition, the term "substituted or unsubstituted heteroaryl group" in the present disclosure also includes substituted or unsubstituted heteroaralkyl group. The term "heteroaralkyl" refers to alkyl moiety which is substituted by heteroaryl wherein the terms alkyl and heteroaryl are as defined above. An example is (2-pyridinyl)ethyl, (3-pyridinyl)ethyl or (2-pyridinyl)methyl. Preferable in this context an alkyl chain contains from 1 to 8 carbon atoms, i.e., 1, 2, 3, 4, 5, 6, 7 or 8, for example, methyl, ethylmethyl, ethyl, propyl, iso-propyl, butyl, iso-butyl, sec-butenyl, tert-butyl, pentyl, hexyl, heptyl, octyl. Heteroaralkyl group is optionally substituted in alkyl and/or heteroaryl part of a group. Preferably, heteroaryl attached to alkyl moiety is oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, 1,2,3-benzotriazinyl, or 1,2,4-benzotriazinyl.

If two or more radicals are selected "independently" of each other, the term "independently" implies that these radicals may be identical or may be different.

Mitochondria Protonophores

The disclosure relates to compounds described by general structure (I) capable of self-regulating mild uncoupling of mitochondria. These compounds concentrate in mitochondria of a living cell at the expense of energy of proton electrochemical potential. This provides accurate, targeted delivery of compounds within a cell, and determines ability of compounds to regulate their concentration inside mitochondria.

The ability of compounds of structure (I) to accumulate in mitochondria depending on membrane potential is associated with a feature of their structure. A general formula of the compounds is as follows:

Structure (I)

"A" is hydrogen, substituted or unsubstituted alkyl, aryl, heteroaryl, cycloalkyl or heterocyclic group; or substituted or unsubstituted aromatic, saturated or partially unsaturated polycyclic system.

"L" is a linker group, comprising substituted or unsubstituted hydrocarbon chain with a length of up to 20 carbon atoms, optionally containing double or triple bonds, heteroatoms, such as —S—, —N—, —O—, or having optional inclusions of groups —C(O)O—, —C(O)—, or —C(O)N(H)—.

"Z" is a positively-charged address group ("Skulachevion") ensuring targeting and delivery of the entire compound into mitochondria. Compounds according to the disclosure also include pharmacologically acceptable anions, solvates, salts, isomers, prodrugs thereof.

The combination of Z, L, and A in one compound of structure (I) ensures penetration of the entire compound into mitochondria; enables accumulation of the compound in mitochondria depending on membrane potential value; and enables the compound to possess protonophore activity or to induce endogenous proton permeability of membranes.

It is preferred to have interaction (in particular, formation of the complex) of entire compound with fatty acid anion in such a way that the resulting form, resulting from such interaction (in particular, the complex of compound of structure I with fatty acid anion) is able to pass through mitochondrial membrane ensuring delivery of fatty acid anion out of the inner mitochondrial membrane (to the intermembrane space).

Preferred compounds of general structure (I) are the following:

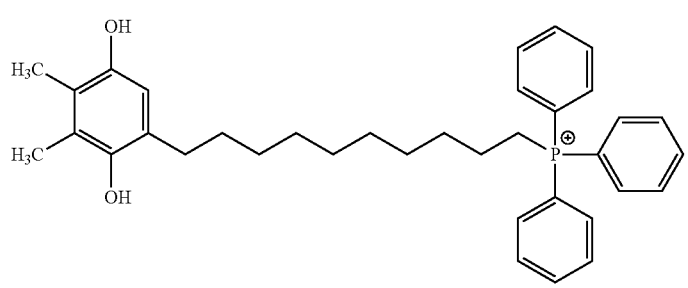

SkQ1

(1)

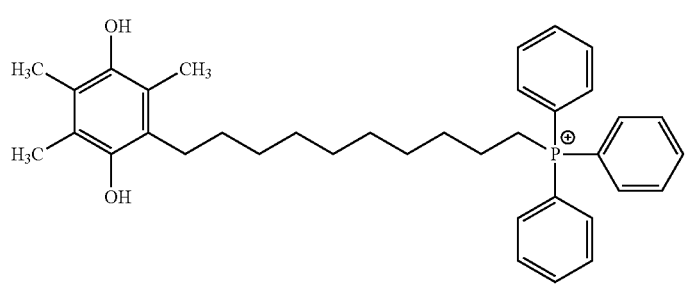

SkQ3

(2)

-continued

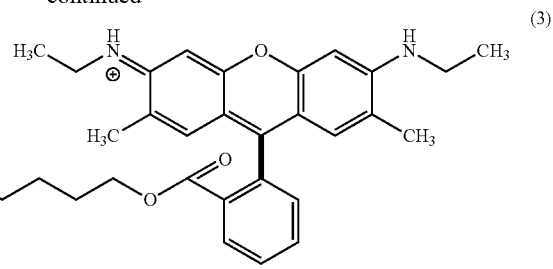

SkQR1 (3)

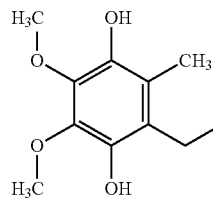 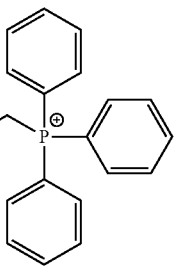

MitoQ (4)

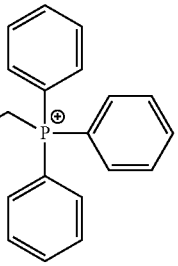

C12TPP (5)

Compounds of structure (I), including the above compounds (1)-(5) (SkQ 1, SkQ3, MitoQ, SkQR1, and C12TPP) are called herein "mitochondria-targeted protonophores."

While not limited to the following, one mechanism of self-regulation of uncoupling activity of compounds of structure (I) is the following. Developed compounds accumulate in mitochondria due to the positive charge of the targeting or "address" part of the molecule according to the Nernst equation, i.e., per every 60 mV of potential, 10-fold accumulation occurs. Being accumulated in mitochondria, compounds increase proton permeability of the inner mitochondrial membrane which stimulates the decrease in membrane potential of mitochondria. The decrease in membrane potential caused by action of developed compounds, in turn, stimulates their exit from the mitochondria, and thus causing a decrease in uncoupling activity. This property of the subject compounds determines their weak uncoupling activity which provides effective uncoupling only of mitochondria with high membrane potential. Most of compounds of structure (I) have antioxidant properties, and thus are able to stabilize biological membranes and preventing their oxidation (see, for example, Skulachev (2007), *Biochemistry (Moscow)*, 72:1385-96; Antonenko, et al. (2008) *J. Membr. Biol.*, 222: 141-9). Thus, such compounds increase insulating properties of membranes and decrease their proton permeability.

Unexpectedly, compounds of structure (I) possess moderate uncoupling activity. This activity is defined by the fact that they comprise a positively-charged group at the expense of which they accumulate in mitochondria. The results of the present experiments indicate that uncoupling properties of these compounds are based on their ability to interact with deprotonated (anionic) forms of fatty acids which stimulates their exit from mitochondria. Mechanism of uncoupling in this case is similar to the physiological one and is based on uncoupling properties of fatty acids. Under physiological conditions, uncoupling of mitochondria occurs due to interaction of fatty acid anion (RCOO$^-$), localized on outer surface of mitochondrial membrane, with proton (H$^+$) which is pumped from mitochondria by respiratory chain enzymes. The resulting protonated form of fatty acid (RCOOH) crosses the membrane and dissociates on its inner surface giving RCOO$^-$ and H$^+$. The latter compensates for the lack of H$^+$ ions inside mitochondria which are removed therefrom by the respiratory chain. This mechanism increases proton permeability of the membrane causing uncoupling of oxidative phosphorylation (FIG. 1). The resulting RCOO$^-$ anion can not get out of mitochondria, itself. Thus, it is this stage which is limiting and which determines the degree of coupling of mitochondrial membrane. Developed compounds are able to accumulate inside mitochondria and bind with fatty acid anions. This binding negates the overall charge of the complex and facilitates its release from mitochondria down the concentration gradient. This mechanism of action explains the high uncoupling activity of compounds of structure (I) which is manifested at concentrations 100-1000 times less (depending on compound) than their detergent properties are manifested. The uncoupling ability of these compounds by this mechanism unexpectedly does not cause violation of physicochemical properties of membranes because mostly hydrophobic, charged compounds of similar structure are strong detergents and stimulate nonspecific and unregulated membrane permeability.

One property of compounds of structure (I) is dependence of their ability to accumulate in mitochondria on membrane potential value. A drop of mitochondrial membrane potential by only 60 mV causes 10-fold decrease in the ability of compounds to accumulate inside mitochondria and prevents their uncoupling activity. The self-regulating efficacy of compounds of structure (I) is one aspect of the present disclosure and may determine high therapeutic activity of the compounds in combination with low toxicity.

The disclosure also provides pharmaceutically acceptable salts of the compounds having structure (I).

The term "pharmaceutically acceptable salt" refers to salt of compound of the present disclosure. Suitable pharmaceutically acceptable salts of compound of the present disclosure include acid addition salts which may be obtained, for example, by mixing solution of compound of the present invention with solution of pharmaceutically acceptable acid, such as hydrochloric acid, sulfuric acid, fumaric acid, maleic acid, succinic acid, acetic acid, benzoic acid, citric acid, tartaric acid, carbonic acid or phosphoric acid. In addition, when compounds according to the disclosure have an acid moiety, their suitable pharmaceutically acceptable salts may include alkali metal salts (e.g., sodium or potassium salts); salts of alkaline earth metals (e.g., calcium or magnesium salts); and salts formed with suitable organic ligands (e.g., ammonium, quaternary ammonium and amine cations formed using counterions, such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium salt of ethylenediaminetetraacetic acid (edetate), camphorate, camphorsulfonate, camsilate, carbonate, chloride, citrate, clavulanate, cyclopentane propionate, digluconate, dihydrochloride, dodecylsulfate, edetate, edisilate, estolate, esilate, ethanesulfonate, formiate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphtoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, theoclate, tosylate, triethiodide, undecanoate, valerate, and the like (e.g., Berge, et al. (1977) *J. Pharm. Sci.*, 66:1-19). Some specific compounds of the present disclosure contain basic and acidic functional groups that allows to convert these compounds into either basic or acid addition salts.

"Neutral" forms of compounds may be recovered by contacting salt with base or acid, with release of the original compound by the traditional way. The original form of a compound differs from various "salt" forms in certain physical properties, such as solubility in polar solvents, but in other aspects, for purposes of the present disclosure, these salts are equivalent to the original form of compound.

In addition to salt forms, the present disclosure provides compounds which are "prodrug" forms of the compound having structure I. Prodrug forms are compounds that under physiological conditions readily undergo chemical changes to form compound of structure (I). A prodrug is pharmacologically active or inactive compound that is chemically modified by physiological action in vivo, such as hydrolysis, metabolism, and the like, to form compound of the present disclosure, after prodrug injection in patient. Additionally, prodrugs can be converted into compounds of the present disclosure by means of chemical or biochemical methods in vitro. For example, prodrugs can be slowly converted into compounds of the present invention under the influence of respective enzyme placed in reservoir transdermal patch. Suitability of method and technique used in obtaining and using prodrugs is well known to those skilled in the art. General consideration of prodrugs which comprise esters is given in a review of Svensson and Tunek, *Drug Metabolism Reviews* (16.5 (1988)) and in Bundgaard, *Design of Prodrugs* (Elsevier (1985)).

Compounds, as well as raw materials for their production according to the disclosure can be synthesized using traditional methods and techniques known to those skilled in the art, i.e., as described in the literature (for example, Houben-Weyl, *Methoden der organischen Chemie*, Georg-Thieme-Verlag, Stuttgart), under reaction conditions which are known to those skilled in the art and which are suitable for these reactions. In addition, in the present disclosure, any other known variants, which are not mentioned here in more detail, may be used.

Some compounds of the present disclosure may exist in unsolvated forms as well as in solvated forms including hydrated forms. In general, solvated forms are equivalent to unsolvated forms and it is assumed that they are within the scope of the present disclosure. Some compounds of the present disclosure may be in various crystalline or amorphous forms. Usually, all physical forms are equivalent for intended use in the present disclosure, and it is assumed that they are within the scope of the present disclosure.

Some compounds of the present disclosure have asymmetric carbon atoms (optical centers) or double-bonds. It is assumed that all "racemates," "enantiomers," "diastereomers," "geometric isomers," and "individual isomers" are within the scope of the present disclosure. Hence, compounds of the disclosure comprise mixtures of stereoisomers, such as mixtures of enantiomers, as well as purified stereoisomers, especially purified enantiomers or stereoisomerically-enriched mixtures, especially enantiomerically-enriched mixtures. In addition, the scope of the disclosure includes individual isomers of compounds shown below by formulas (1) to (5), as well as any of their fully or partially balanced mixtures. In addition, the present disclosure comprises individual isomers of compounds shown below by formulas, as mixtures with isomers thereof in which one or more chiral centers are inverted. In addition, it should be understood that all tautomers and mixtures of tautomers of compounds of formulas (1)-(5), are within the scope of compounds of formulas (1)-(5), and preferably match formula and partial formula which meet this goal.

Obtained racemates can be split into isomers by essentially known mechanical or chemical ways. Diastereomers are preferably formed from racemic mixture by means of intereaction with optically active splitting agent. The splitting of enantiomer with the use of a column filled with optically active splitting agent is also advantageous.

In addition, the splitting of diastereomer can be accomplished using standard purification methods, for instance, such as chromatography or fractional crystallization. Compounds of the present disclosure may also have unnatural ratios of atomic isotopes for one or more atoms which are part of such compounds. For example, these compounds can be labeled with radioactive isotopes, such as tritium ($^3$H), iodine-125 ($^{125}$I) or carbon-14 ($^{14}$C). It is assumed that all isotopic variants of compounds of the present disclosure (radioactive or not radioactive) are within the scope of protection of the present invention.

Embodiments include: alkoxy, cycloalkoxy, aryloxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, and alkynylamino radicals.

Other embodiments include radicals: hydroxyalkyl, hydroxycycloalkyl, hydroxyaryl, hydroxyaralkyl, hydroxyalkenyl, hydroxycycloalkenyl, hydroxyalkynyl, mercaptoalkyl, mercaptocycloalkyl, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, and aminoalkynyl radicals.

In another embodiment, hydrogen atoms in alkyl, cycloalkyl, aryl, aralkyl, alkenyl, cycloalkenyl, alkynyl radicals may be substituted independently of each other by one or more halogen atoms. One representative radical is a trifluoromethyl radical.

Pharmaceutical compositions comprising an effective amount of mitochondria-targeted protonophore compounds of structure (I) and a pharmaceutically acceptable carrier are also provided. These compositions are intended to prevent or treat certain diseases, for which mild uncoupling of mitochondria of an organism is effective. The medical purpose of the compositions is largely determined by content, dosage, and mode of application etc.

A further aspect of the present disclosure is use of mitochondria-targeted protonophores for preventing or treating diseases, for which stimulation of cellular metabolism by means of mitochondria-targeted protonophores is effective.

Another aspect of the present disclosure is use of mitochondria-targeted protonophores for preventing or treating cardiovascular pathologies including atherosclerosis, cardiac arrhythmias, ischemic heart disease, myocardial infarction, renal ischemia or infarction, brain stroke, and various diseases and pathological conditions resulting from disorders of blood circulation or oxygen supply to tissues and organs.

Other aspects of the present disclosure include the application of mitochondria-targeted protonophores for treatment of pathological conditions that are consequences of non-ischemic circulatory disorders, including consequences of hemorrhagic hypovolemia caused by destruction of vessels or violation of their permeability, and also hypovolemia caused by vasodilators.

Yet another aspect is the application of mitochondria-targeted protonophores for treatment of pathological conditions that are consequences of non-ischemic circulatory disorders including hypovolemia caused by loss of water through skin, lungs, gastrointestinal tract or kidneys, including hypovolemia provoked by diuretics.

Still another aspect of the disclosure is the application of mitochondria-targeted protonophores for treatment of consequences of hypoxemic hypoxia caused by lack of oxygen in arterial blood, including hypoxia caused by lack of oxygen in inhaled air. Alternatively, the mitochondria-targeted protonophores are useful for treatment of consequences of anemic hypoxia caused by decrease in blood oxygen capacity by virtue of the fall of the amount of hemoglobin in blood or a change in hemoglobin's state.

Another aspect is the application of mitochondria-targeted protonophores for prevention of development or treatment of unwanted changes in cells, tissues or organs, natural blood flow or oxygen supply to which is limited or terminated during medical intervention including during apheresis, reducing or eliminating blood flow to cells, tissues or organs aimed at their further conservation and/or transplantation, as well as various surgical procedures.

Yet another aspect of the disclosure is the application of mitochondria-targeted protonophores for increase in lifespan of a human or an animal, as well as at disease associated with aging and increased oxidative stress.

Still another aspect is the application of mitochondria-targeted protonophores to combat eye diseases associated with oxidative stress and/or massive loss of retinal cells or other types of cells involved in processes for ensuring vision.

Other aspects of the disclosure is the application of mitochondria-targeted protonophores for: the treatment or prevention of diseases associated with massive programmed cell death in tissues and organs and/or associated with distribution of signals in affected tissue which trigger programmed cell death; the prevention and/or treatment of cardiovascular diseases for which the key role of programmed cell death, apoptosis or necrosis; the transplantation to combat tissue rejection and preserve graft material; cosmetology and surgery to overcome effects of burns, improve healing of wounds and surgical sutures; biotechnology to increase viability of animal cell culture or human cell culture for research and technological needs; and to increase productivity of animal, human, plant or fungal cell culture, when used for production of compounds, pharmaceutical preparations, proteins, or antibodies.

The mitochondria-targeted protonophores are also useful to increase productivity of whole plants, when used for production of compounds, pharmaceutical preparations, proteins, or antibodies. They can also be used to increase productivity of a cell culture of yeast and other fungi of genera *Saccharomyces, Pichia, Hansenula, Endomyces, Yarrowia*, when used for the production of compounds, pharmaceutical preparations, proteins, or antibodies. Additionally, they can be used to increase viability of a plant protoplast culture, when used for production of compounds, pharmaceutical preparations, proteins, or antibodies, or for the production of genetically modified plants, for example, to increase viability of regenerating plants, callus cells.

"Diseases associated with disorders of cell metabolism" refer to insulin-dependent diabetes mellitus, insulin-dependent diabetes mellitus with coma, insulin-dependent diabetes mellitus with ketoacidosis, insulin-dependent diabetes mellitus with renal disease, insulin-dependent diabetes mellitus with eye damage, insulin-dependent diabetes mellitus with neurological complications, insulin-dependent diabetes mellitus with peripheral circulatory disorders, insulin-dependent diabetes mellitus with multiple complications, insulin-dependent diabetes mellitus without complications, non-insulin-dependent diabetes mellitus, non-insulin-dependent diabetes mellitus with coma, non-insulin-dependent diabetes mellitus with ketoacidosis, non-insulin-dependent diabetes mellitus with renal disease, non-insulin-dependent diabetes mellitus with eye damage, non-insulin-dependent diabetes mellitus with neurological complications, non-insulin-dependent diabetes mellitus with peripheral circulatory disorders, malnutrition-related diabetes mellitus, localized fat deposition, obesity, obesity caused by excessive energy intake, obesity caused by taking drugs, extreme obesity accompanied by alveolar hypoventilation, hypervitaminosis A, hypercarotinemia, vitamin B6 overdose syndrome, hypervitaminosis D, effects of excess food supply, disorders of aromatic amino acid metabolism, classic phenylketonuria, other types of hyperphenylalaninemia, disorders of tyrosine metabolism, albinism, other disorders of aromatic amino acid metabolism, disorders of branched-chain amino acid metabolism and fatty acid metabolism, maple syrup urine disease, violation of transport of amino acids, disorders of sulfur-containing amino acid metabolism, urea cycle disorders, disorders of lysine and hydroxylysine metabolism, disorders of ornithine metabolism, disorders of glycine metabolism, lactose intolerance, inborn lactose deficiency, secondary lactase deficiency, glycogen storage diseases, disorders of fructose metabolism, disorders of galactose metabolism, disorders of pyruvate metabolism and gluconeogenesis, disorders of sphingolipid metabolism and other lipid storage diseases, GM2-gangliosidosis, sphingolipidosis, neuronal ceroid lipofuscinoses, disorders of glycosaminoglycan metabolism, mucopolysaccharidosis type I, mucopolysaccharidosis type II, disorders of glycoprotein metabolism, defects in post-translational modification, disorders of glycoprotein degradation, pure hypercholesterolemia, pure hyperglyceridemia, mixed hyperlipidemia, hyperchylomicronaemia, lipoprotein deficiency, disorders of purine and pyrimidine metabolism, hyperuricemia without signs of inflammatory and gouty arthritis, Lesch-Nyhan syndrome, disorders of porphyrin and bilirubin metabolism, hereditary erythropoietic porphyria, porphyria cutanea tarda, defects of catalase and peroxidase, Gilbert's syndrome, Crigler-Najjar Syndrome, disorders of mineral metabolism, cystic fibrosis, amyloidosis, hyperosmolarity and hypernatremia, hypoosmolarity and hyponatremia, acidosis, alkalosis, nutrition disorders, and metabolic disorders in other diseases.

"Ischemic heart disease" refers to angina [angina pectoris], unstable angina pectoris, unstable angina pectoris with hypertension, angina pectoris with documented spasm, angina pectoris with documented spasm with hypertension, acute myocardial infarction, acute transmural anterior wall myocardial infarction, acute transmural anterior wall myocardial infarction with hypertension, acute transmural inferior wall myocardial infarction, acute transmural inferior wall myocardial infarction with hypertension, acute subendocardial myocardial infarction, acute subendocardial myocardial infarction with hypertension, recurrent myocardial infarction, recurrent inferior wall myocardial infarction, some current complications following acute myocardial infarction, hemopericardium as current complication following acute myocardial infarction, atrial septal defect as current complication following acute myocardial infarction, ventricular septal defect as current complication following acute myocardial infarction, thrombosis of atrium, auricular appendage, and ventricle as current complications following acute myocardial infarction, other forms of acute ischemic heart disease, coronary thrombosis that does not lead to myocardial infarction, Dressler's syndrome, Dressler's syndrome with hypertension, chronic ischemic heart disease, atherosclerotic cardiovascular disease, old myocardial infarction, cardiac aneurysm, cardiac aneurysm with hypertension, coronary artery aneurysm, coronary artery aneurysm with hypertension, ischemic cardiomyopathy, and asymptomatic myocardial ischemia.

Other heart diseases refer to acute pericarditis, acute nonspecific idiopathic pericarditis, infectious pericarditis, chronic adhesive pericarditis, chronic constrictive pericarditis, pericardial effusion (noninflammatory), acute and subacute endocarditis, acute and subacute infective endocarditis, non-rheumatic mitral valve lesions, mitral valve insufficiency, mitral valve prolapse, non-rheumatic mitral valve stenosis, non-rheumatic aortic valve lesions, aortic valve stenosis, aortic valve insufficiency, non-rheumatic tricuspid valve lesions, non-rheumatic tricuspid valve stenosis, non-rheumatic tricuspid (valve) insufficiency, pulmonary valve lesions, pulmonary valve stenosis, pulmonary valve insufficiency, pulmonary valve stenosis with insufficiency, acute myocarditis, infectious myocarditis, isolated myocarditis, cardiomyopathy, dilated cardiomyopathy, obstructive hypertrophic cardiomyopathy, eosinophilic endomyocardial disease, endocardial fibroelastosis, alcoholic cardiomyopathy, cardiomyopathy caused by the influence of drugs and other external factors, atrioventricular block and left bundle branch (the His bundle) block, first-degree atrioventricular block, second-degree atrioventricular block, third-degree atrioventricular block (complete heart block), pre-excitation syndrome, cardiac arrest, cardiac arrest with successful restoration of cardiac activity, paroxysmal tachycardia, recurrent ventricular arrhythmia, supraventricular tachycardia, ventricular tachycardia, atrial fibrillation and atrial flutter, ventricular fibrillation and ventricular flutter, premature atrial depolarization, premature ventricular depolarization, sick sinus syndrome, heart failure, congestive heart failure, left ventricular failure, and myocardial degeneration.

"Stroke" refers to both hemorrhagic and ischemic brain strokes, and their symptoms.

"Renal ischemia" or "renal infarction" refers to periarteritis nodosa, Wegener's granulomatosis, hemolytic-uremic syndrome, idiopathic thrombocytopenic purpura, syndrome of disseminated intravascular coagulation (DIC), renal artery ischemia or renal artery infarction (extrarenal part), renal atherosclerosis, congenital renal stenosis, Goldblatt kidney, acute nephritic syndrome, minor glomerular disorders, focal and segmental glomerular lesions, diffuse membranous glomerulonephritis, diffuse mesangial proliferative glomerulonephritis, diffuse endocapillary proliferative glomerulonephritis, diffuse mesangiocapillary glomerulonephritis, dense deposit disease, diffuse crescentic glomerulonephritis, rapidly progressive nephritic syndrome, recurrent and persistent hematuria, chronic nephritic syndrome, and nephrotic syndrome, and nephritic syndrome.

"Different eye pathologies" refer to different forms of macular degeneration (MD) and other related symptoms such as: atrophic (dry) MD, exudative (wet) MD, age-related maculopathy (ARM), choroidal neovascularization, detached pigment retinal epithelium (PED), atrophy of pigment retinal epithelium (RPE). The term "macular degeneration (MD)" also comprises all eye diseases irrelevant to age-related changes in a human organism such as vitelliform degeneration of Best, Stargardt disease, juvenile macular dystrophy, Behr's disease, Sorsby's dystrophy, Doyne honeycomb retinal dystrophy. Symptoms related to macular degeneration refer to: drusen surrounded by white-yellow spots, submacular discoid scar of tissues, choroidal neovascularization, detached pigment retinal epithelium (PED), atrophy of pigment retinal epithelium (RPE), anomalous expansion of choroidal blood vessels, blurred or disturbed vision area, central dead point, pigment anomalies, mixed layer of thin granulation located on the inner side of Bruch's membrane, thickening and lowered permeability of Bruch's membrane. The causes of macular degeneration include, but are not limited to: genetic or physical trauma, diseases such as diabetes, or infections, in particular, bacterial infection.

"Wounds" and other "surface injuries" refer to wounds associated with damage of skin epithelium, corneal epithelium, surfaces of the gastrointestinal tract, pulmonary epithelium and inner surfaces of liver vessels, blood vessels, uterus, vagina, urethra, or respiratory tract and also wounds and other surface damage associated with prolonged epithelial defects and recurrent epithelial erosions, such as: surgical wounds, excision wounds, blisters, ulcers, other lesions, abrasions, erosions, lacerations, cuts, suppurating wounds, boils and thermal or chemical burns. Wounds can be caused by mechanical damage, and result from other diseases, such as: diabetes, corneal dystrophy, uremia, malnutrition, vitamin deficiency, obesity, infection, immunodeficiency, or complications associated with systematic use of steroids, radiation therapy, non-steroidal anti-inflammatory drugs, and anticancer drugs.

Application of pharmaceutical compositions related to the present disclosure can be both somatic and local. Procedures of administration comprise enteral, such as oral, sublingual and rectal; local, such as transdermal, intradermal and oculodermal; and parenteral. Suitable parenteral procedures of administration comprise injections, for example, intravenous, intramuscular, subdermal, intraperitoneal, intra-arterial, and other injections, and non-injecting practices, such as vaginal or nasal, as well as procedure of administration of a pharmaceutical composition as angioplastic stent coating. Preferably, compounds and pharmaceutical compositions related to the present invention, are for intraperitoneal, intravenous, intra-arterial, parenteral or oral administration. In particular, administration can be given in form of injections or tablets, granules, capsules, or other pressed or compressed form.

When a compound of structure (I) is administered as a pharmaceutical composition, a compound of structure (I) should be mixed according to formula with a suitable amount of pharmaceutically acceptable solvent or carrier so that to have the appropriate form for administration to a patient. The term "solvent" relates to diluent, auxiliary medicinal substance, filler or carrier which is mixed with a compound of structure (I) for administration to a patient. Liquors like water, and oils including petrolic, animal, vegetative and synthetic, such as peanut oil, soybean oil, mineral oil and other similar oils can be used as said pharmaceutical carriers. Normal saline solution, acacia pitch, gelatin, starch, talc, keratin, colloid silver, urea etc can serve as said pharmaceutical solvents. The composition can also comprise auxiliary substances, stabilizers, thickeners, lubricant, and coloring agents.

Compounds and compositions related to the present disclosure can be administered in form of capsules, tablets, pills, pillets, granules, syrups, elixirs, solutions, suspensions, emulsions, suppositories or retarded release substances, or in any other form suitable for administration to a patient. One embodiment of the present disclosure is application of compounds of structure (I) and compositions in form of solutions for oral and intraperitoneal, intra-arterial, and intravenous administration.

Therapeutically effective amount of a pharmaceutical composition comprising a compound of structure (I) required for treatment of a specific disease or symptom, depends on the nature of disease or symptom and a procedure of administration and should be determined at consultation with a physician in charge. Acceptable doses of the compound of structure (I) for oral administration are from 0.025 microgram to about 120 milligrams per kg of patient body weight, about 25 micrograms per kg of patient body weight is more preferable, or about 50 micrograms per kg of patient body weight is the most preferable. Acceptable doses for intravenous administration are from about 0.1 microgram to about 100 milligrams per kg of patient body weight, about 25 micrograms per kg of patient body weight is more preferable, or about 125 micrograms per kg of patient body weight is the most preferable.

For optimal protection of cells, tissues and organs, compound of structure (I) as a pharmaceutical composition is administered 6-48 hours (or 24 hours) before ischemic exposure.

Reference will now be made to specific examples illustrating the invention. It is to be understood that the examples are provided to illustrate certain embodiments and that no limitation to the scope of the invention is intended thereby.

EXAMPLES

Example 1

Synthesis of C12-TPP

To synthesize dodecyl triphenylphosphonium, scheme of synthesis comprising alkylation of triphenylphosphine (2) with dodecyl iodide (1) with subsequent conversion of resulting dodecyl triphenylphosphonium iodide (3) to corresponding base (4) and then to chloride (5) was proposed (Scheme 1).

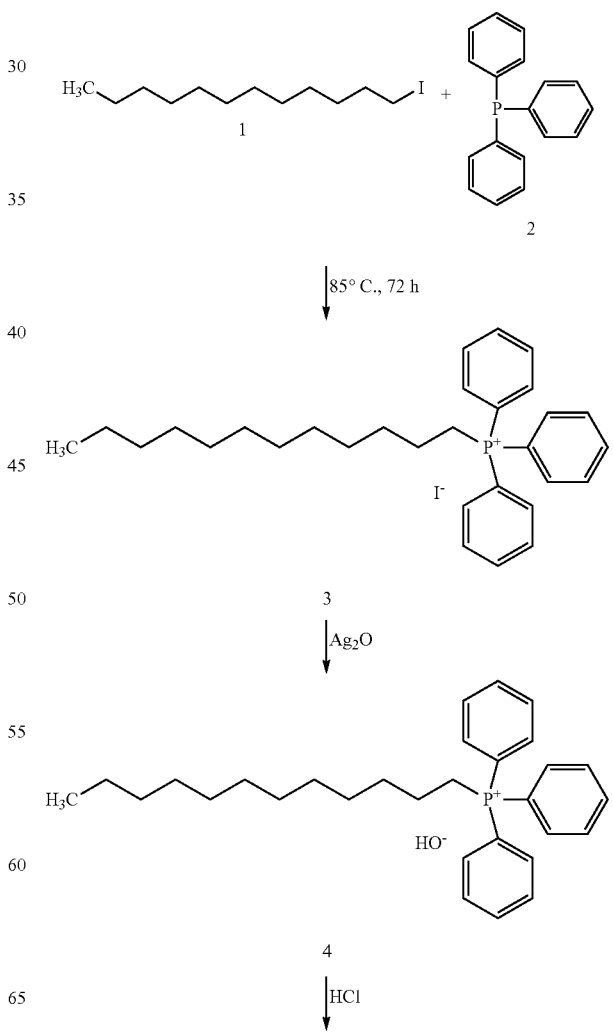

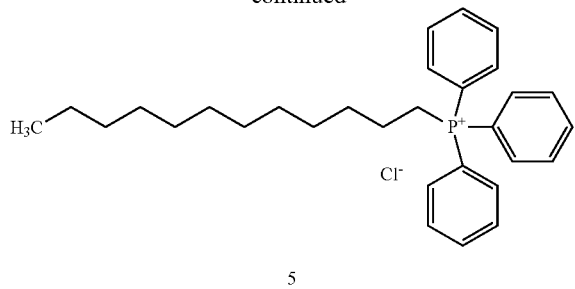

5

Synthesis of dodecyl triphenylphosphonium iodide (3) is as follows: 359 μl (430.4 mg, 1.6 mmol) of dodecyl iodide (Acros Organics, Geel, Belgium) and 466 mg (1.7 mmol, 10% excess) of triphenylphosphine in 2.5 ml of 96% ethanol were kept in a sealed tube for 72 hours at 85-90° C. The reaction mixture was evaporated to dryness, the residue was chromatographed on silica gel column with chloroform:methanol (9:1). Yield: 882 mg (99%).

Synthesis of dodecyl triphenylphosphonium chloride (5) is as follows: 68 mg (0.12 mmol) of dodecyl triphenylphosphonium iodide (Aldrich, Moscow, Russia) (3) was dissolved in 500 μl of methanol, 100 mg of wet freshly prepared silver oxide was added to the solution. The sediment was centrifuged, 1 N hydrochloric acid was added to the supernatant until acidic reaction (120 μl), evaporated to dryness, the residue was washed with water. Yield: 35 mg (62.5%). Purity of the product by HPLC is 100%; m/z (found/calculated): 431.4/431.6.

At the first stage, yield of product 3 is quantitative, after conversion of resulting compound to chloride 5, yield is over 60%.

Thin layer chromatography (TLC) on Kieselgel 60 F254 plates (Merck) was used for analysis. Compounds comprising groups which absorb in the UV region were detected by Brumberg chemiscope.

Ultraviolet absorption spectra were recorded using a Varian Cary 50 Bio spectrophotometer. Reversed phase HPLC was performed using an Agilent 1100 chromatograph.

Mass spectrometry analysis of these compounds was performed by ionspray mass spectrometer Bruker. PMR and $C^{13}$-NMR. Proton (PMR) spectra of solutions of compounds in $CDCl_3$ were recorded at 303 K using a Bruker DRX-500 spectrometer operating at a frequency of 500.13 MHz for proton. $C^{13}$-NMR carbon spectra (proton decoupled) was performed using a Bruker AM-300 spectrometer operating at a frequency of 75.43 MHz for $^{13}C$. Multiplicity of signals in the $^{13}C$ spectra was determined using the INEPT technique. The residual signal of chloroform ($\delta_H$ 7.27, $\delta_C$ 77.0) was used as an internal standard.

Figure 2:
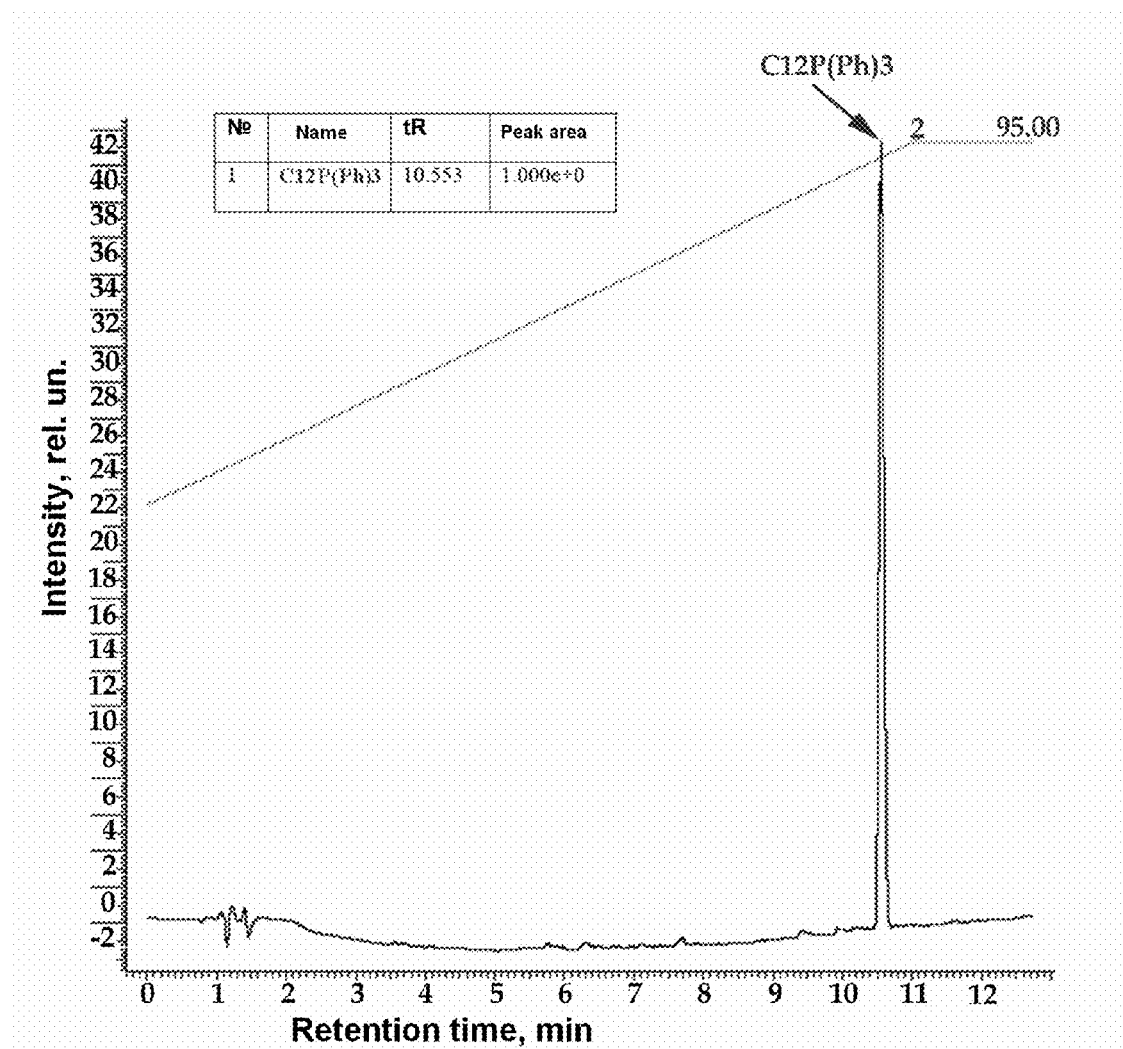
FIG. 2 is a graphic representation of an HPLC chromatogram of dodecyl triphenylphosphonium.
Figure 3:
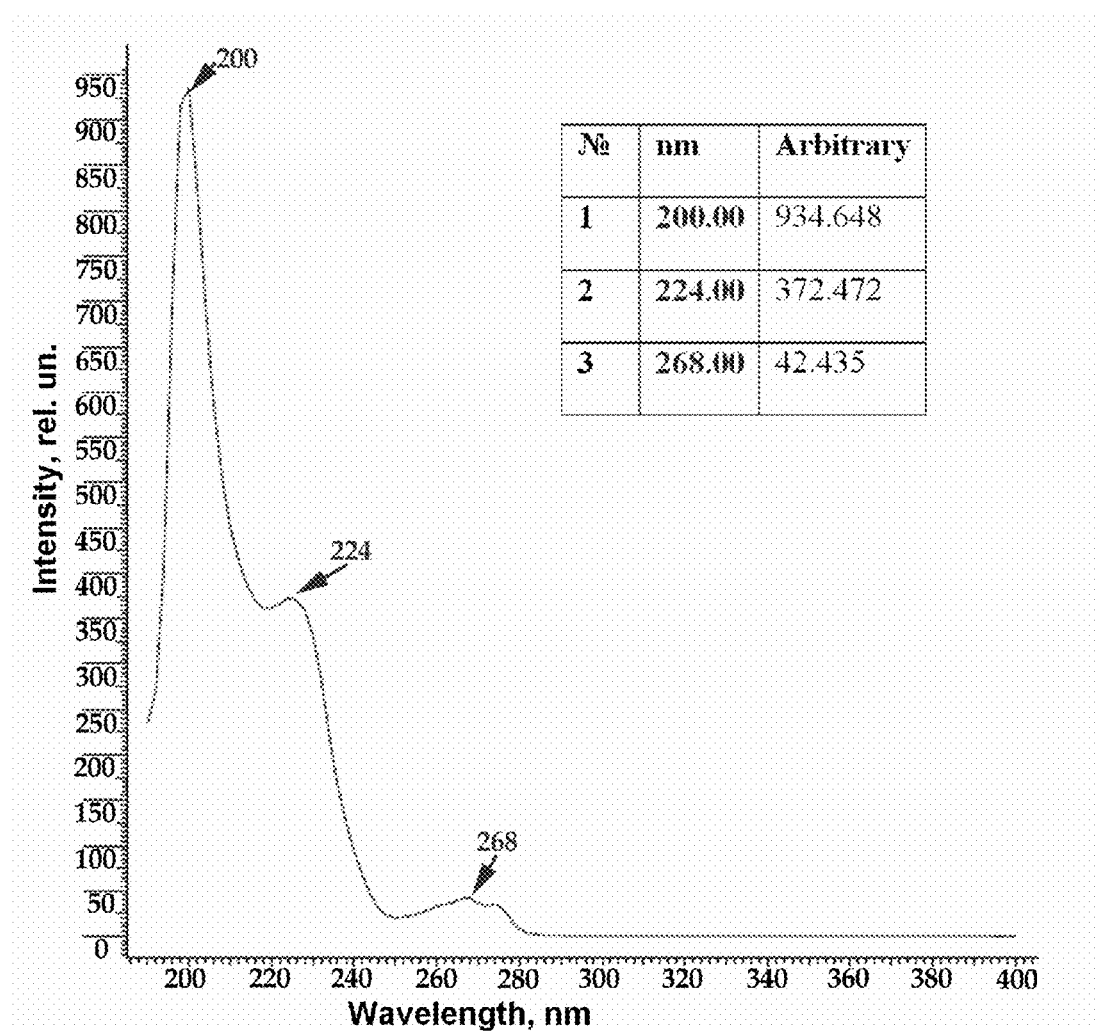
FIG. 3 is a graphic representation of the UV spectrum of dodecyl triphenylphosphonium.
Figure 4:
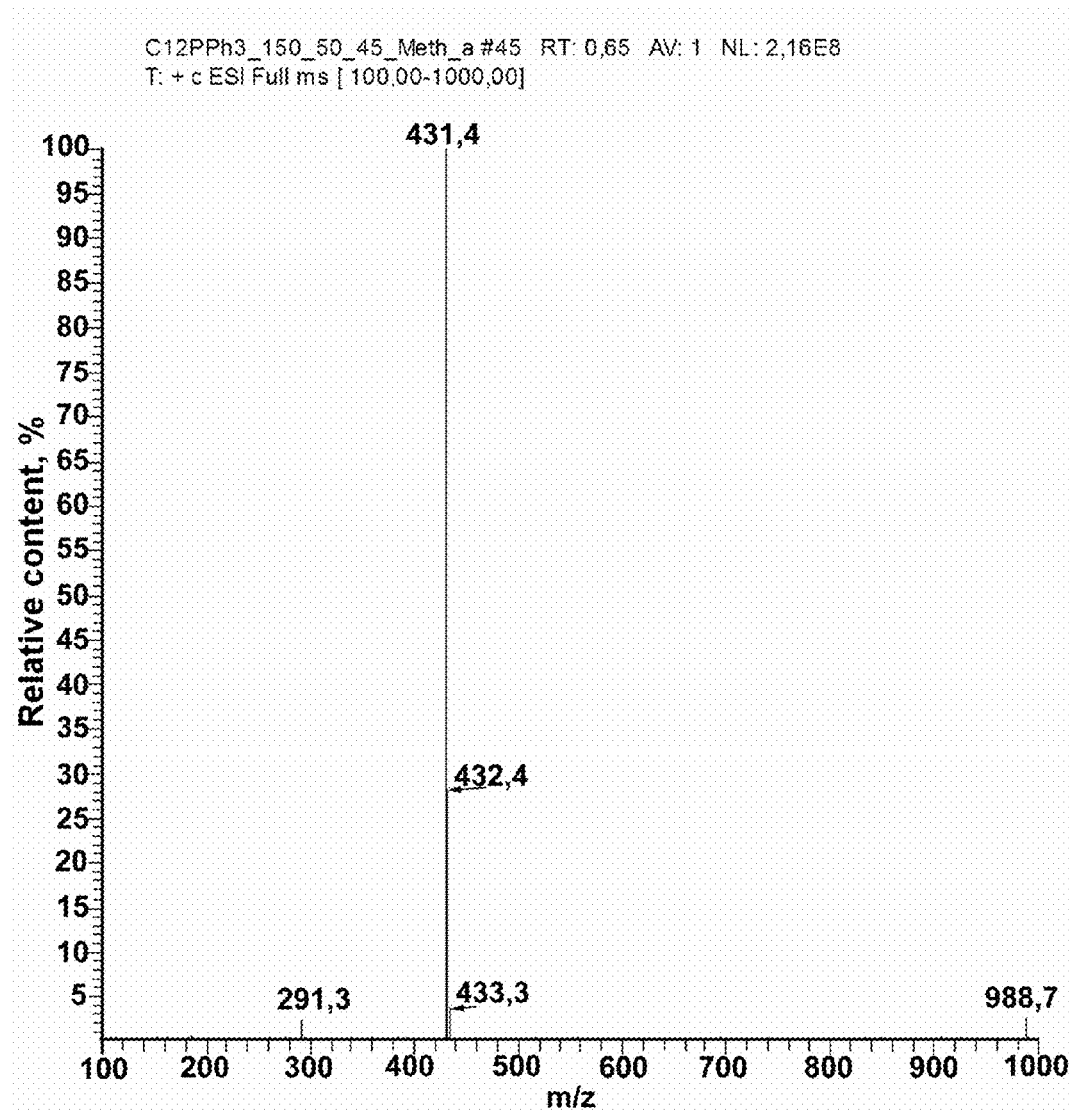
FIG. 4 is a graphic representation of the mass spectrum (ESI-MS) of dodecyl triphenylphosphonium.

FIGS. 2, 3 and 4 show HPLC chromatograms, UV, and mass spectra, respectively, of the resulting derivative.

Example 2

Protonophore Activity of C12-TPP on "Black Membrane" Model

To test penetrating ability of mitochondria-targeted compounds of structure (I), a method based on the ability of ions to penetrate through the bilayer phospholipid membrane moving along concentration gradient was used. The two chambers filled with an aqueous solution are separated by the bilayer membrane, the compound tested is added to one of the chambers. If a charged compound is capable of penetrating through the bilayer membrane, fast diffusion of the compound from the chamber with its high concentration to the chamber with its low concentration occurs, thus difference in the potentials is formed on the membrane. For ions carrying one charge and capable of passive penetrating through the membrane, the 10-fold concentration gradient allows to produce the potential of 60 mV (according to the Nernst equation).

This method was used in various studies on the ability of ions to penetrate through a bilipid membrane and is described in Starkov, et al. (1997) *Biochem. Biophys. Acta,* 1318:159-172. With this method, C12-TPP (compound of structure (I)) was tested.

Figure 5:
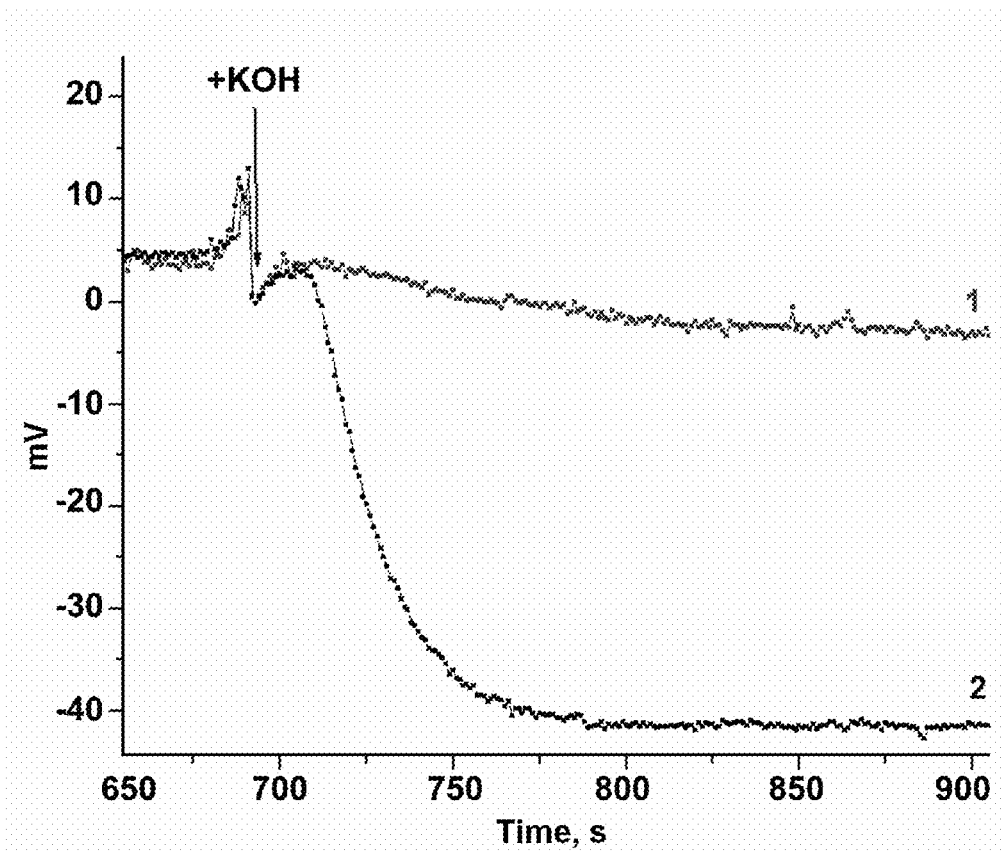
FIG. 5 is a graphic representation of change of diffusion potential ($\Delta\Psi$) on lipid bilayer formed from lipid diphytanoyl (20 mg/ml) showing the absence of palmitic acid in the membrane (curve 1) and in the presence of palmitic acid in the membrane at a concentration of 1 mg/ml (curve 2) induced by addition of KOH in the presence of penetrating cation C12.

FIG. 5 shows results of measurement of diffusion potential (ΔΨ) on lipid bilayer formed from lipid diphytanoyl in the absence of palmitic acid in the membrane (curve 1) and in the presence of palmitic acid in the membrane at a concentration of 1 mg/ml (curve 2) induced by addition of KOH in the presence of penetrating cation C12-TPP. Experiments were carried out in a Teflon cuvette having two compartments, and in a 0.6-mm hole between the two compartments the membrane was formed. Medium contained 50 mM Tris-HCl, 100 mM KCl, pH=7.5. ΔpH=1 was created by adding KOH to one of the cuvette compartments. Penetrating cation C12-TPP at a concentration of 1 μM was added to both compartments of the cuvette.

As can be seen in FIG. 5, the presence of a fatty acid in the membrane facilitates an increase in diffusion potential in response to ΔpH creation. This result points to dependence of protonophore activity of C12-TPP on the presence of a fatty acid in the membrane.

Example 3

Effect of Fatty Acid on Micelles Formed by SkQR1 in Aqueous Solution Using Fluorescence Correlation Spectroscopy Fluorescence correlation spectroscopy (FCS) is often used to study micellization of surfactants. In one report (Lu, et al. (2006) *Analytica Chimica Acta,* 556:216-225), R18, i.e., rhodamine with covalently attached fat tail was used as a marker. R18 itself forms large and poorly fluorescent aggregates in aqueous solution resulting in a small number of particles in the confocal volume (N) and a small fluorescence signal. When a detergent was added at a concentration above its CMC (the critical micelle concentration), an increase in total fluorescence and a significant increase in the number of particles N occurred. Correlation time τ also decreased that can be estimated by the time where autocorrelation function decreased by half as compared to a maximum value. That was associated with lower diffusion coefficient of detergent micelles as compared to the R18 aggregates.

Figure 6A:
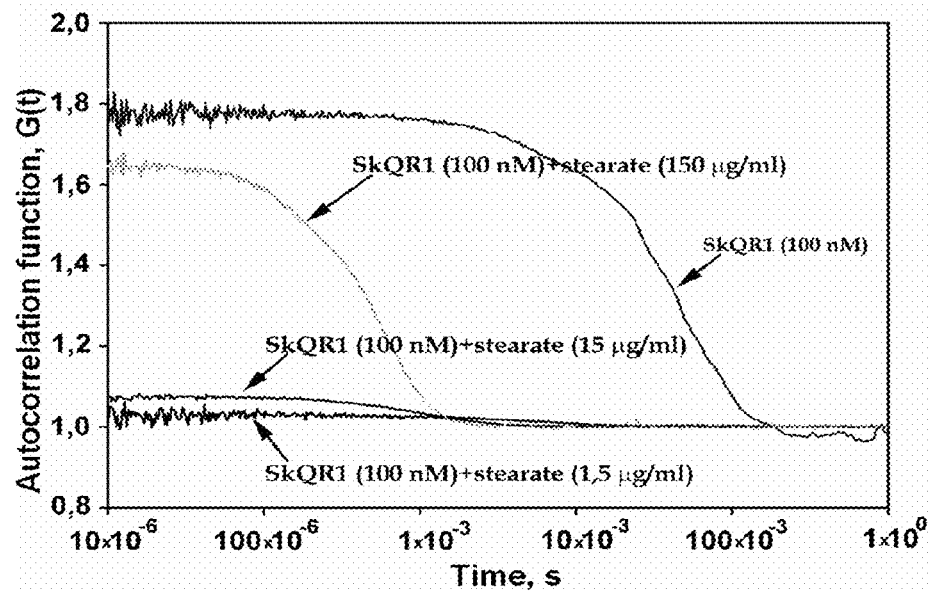
FIG. 6A is a graphic representation of fluorescence correlation spectroscopy data showing the effect of fatty acid (stearate) on autocorrelation function of SkQR1 in water.
Figure 6B:
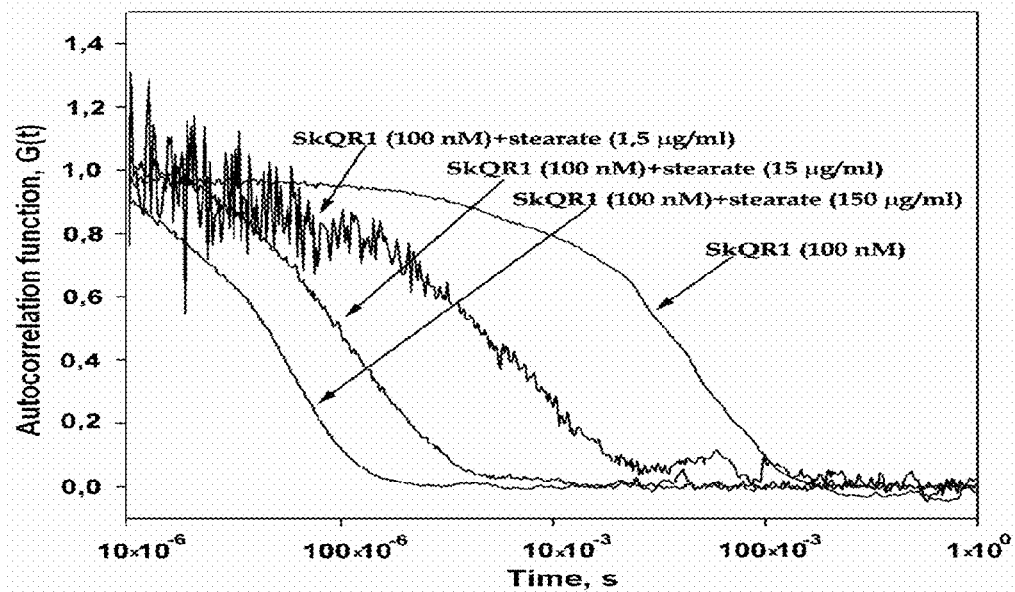
FIG. 6B is a graphic representation of fluorescence correlation spectroscopy data showing normalized autocorrelation functions which can be used for estimation of correlation time of fluctuations of fluorescence.

FIGS. 6A and B show the effect of a fatty acid (stearate) on the autocorrelation function of SkQR1 in water. These fluorescence correlation spectroscopy data enables one to measure diffusion coefficient (D) of fluorescent molecules or complexes (see, Hess, et al. (2002) *Biochem.* 41:697-705. The value of D can be derived from this figure by fitting the dependence of G (tau) on tau. G (tau is a autocorrelation transformation of the dependence of fluorescence signal on time. FIG. 6B (bottom panel) shows normalized data in such a way that the autocorrelation function in the small-time limit is equal to unity). In the absence of stearate, fluorescence signal from the sample was 44 kHz. Addition of 1.5 μg/ml (about 5 μM) stearate increases the signal (67 kHz) and sharply decreases the value of the autocorrelation function. For example, the number of particles in the confocal volume sharply increases. The constant of micelle formation for stearate is about 0.3 mM. In this case, fragmentation of the SkQR1 aggregates induced by such low concentrations of the fatty acid occurs. This fragmentation decreases the degree of the self-quenching of fluorescence that increases the total signal. The increase in a concentration of stearate up to 50 µM increases the amplitude of the autocorrelation function that may suggest the beginning of the micellization process of stearate in the presence of SkQR1. The constant of micelle formation for anionic surfactants decreases under the influence of cationic surfactants or polymers. In that case, the total fluorescence signal was 141 kHz. A further increase in a concentration of stearate causes even a larger growth of the autocorrelation function (a decrease in the number of particles), that suggests the completion of the micellization process of stearate and inclusion of SkQR1 in the micelles. The total fluorescence signal was 63 kHz that points to the beginning of the self-quenching of the dye in the micelles.

FIG. 6A shows normalized autocorrelation functions which can be used for estimation of correlation time of fluctuations of fluorescence. Typically, these fluctuations can be associated with the diffusion of particles and these data are used to determine diffusion coefficients. The control curve (black) with rhodamine 6G shows fit of diffusion curve that describes the experimental data very well. The same panel shows fit of curve for the red curve (i.e., SkQ 1+Stearate, dark gray curve). In this case, the theoretical equation describes these data very poor. The fluctuations of the fluorescence signal in this case have no diffusion component yet. This process may be the output/input of SkQR1 molecules from water into micelles that can lead to fluctuations of the fluorescence due to the different quantum yield of fluorescence of the dye in polar and non-polar environments (Zettl, et al. (2005) *J. Phys. Chem. B*. 109:13397-13401).

This study shows that SkQR1 forms micelles (or large aggregates) in aqueous solution which can degrade in the presence of low concentrations of fatty acids, suggesting the interaction of these two compounds.

Example 4

Effect of Compounds of Structure (I) on Programmed Death in Yeast Induced by Amiodarone Amiodarone (a calcium channel blocker) causes the death of the yeast *Saccharomyces cerevisiae* which by a number of features resembles apoptosis in higher eukaryotes. In the cells, amiodarone induces activation of a cascade of events leading to formation of reactive oxygen species and subsequent cell death. Addition of antioxidants alpha-tocopherol and N-acetylcysteine partially prevented cell death under these conditions (Pozniakowsky, et al. (2005) *J. Cell. Biol.* 168:257-269). A source of formation of reactive oxygen species induced by amiodarone is a hyperpolarized mitochondrium.

In this study, the effectiveness of compounds of structure (I) possessing uncoupling properties in this system was evaluated. The following compounds of structure (I) (SKQ1, SKQ3, and C12TPP) were selected for this study. Yeast cells were grown in rich liquid medium YPD (2% bactopepton, 2% glucose, and 1% yeast extract) to cell density approximately 2*106 cells/ml. Then a compound of structure (I) or mock and 80 µM amiodarone were added to the cell suspension. Cells were incubated for 1 hr at 30° C. and afterwards transferred to solid YPD medium containing 2% bactoagar. The number of colonies was counted after 2 days of incubation on solid medium. 100% survival corresponds to the number of colonies from zero time-point transferred to solid medium prior to addition of amiodarone.

Figure 7:
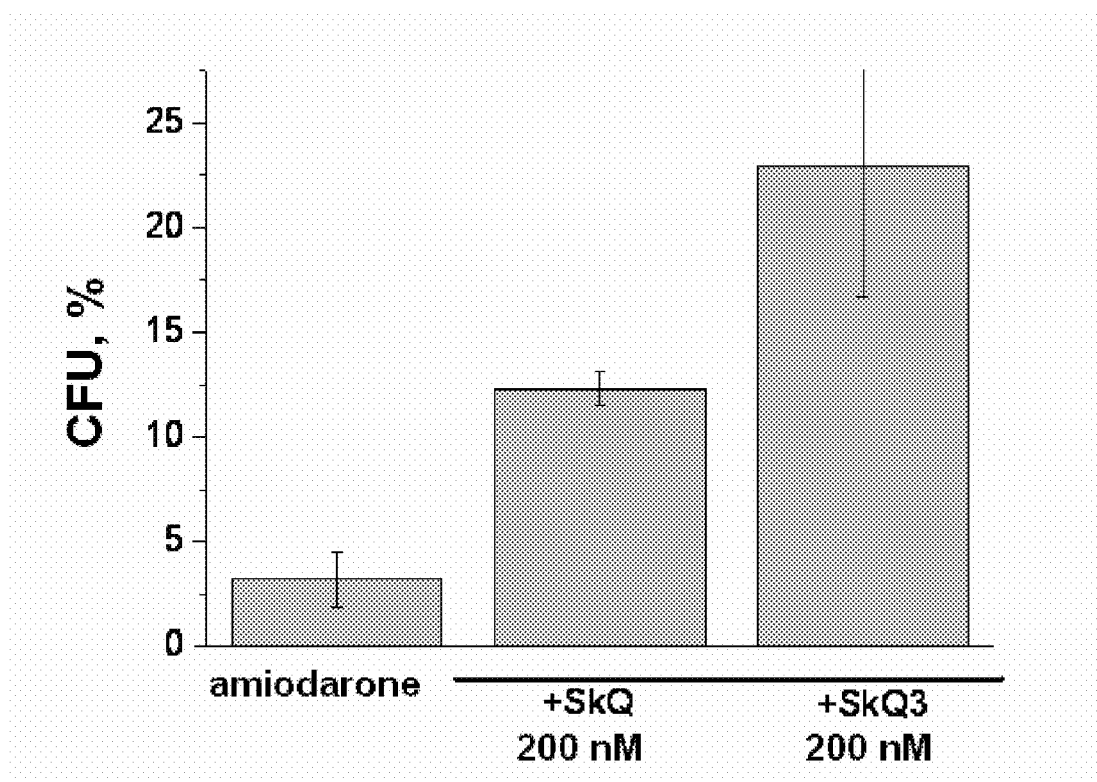
FIG. 7 is a graphic representation of the cell viability of yeast cells exposed to amiodarone (80 µM) in CFU which shows the comparison of the protective effect of SkQ and SkQ3.

The results show that SkQ1 and SkQ3 significantly increase the survival of cells in the presence of amiodarone (FIG. 7). SkQ3 was somewhat more effective but the differences in the strength of the effects of these two antioxidants were not statistically significant. SkQR1 and MitoQ also increased the survival of yeast cells in the presence of 80 µM amiodarone from 2 to 7 and from 2 to 8 percent, respectively. (3 independent experiments were performed for each condition, at least 100 colonies were grown for each zero point, calculated p-value—below 0.05.)

The protective effect of the SkQ derivatives may be due to not only their direct antioxidant properties from the quinone moiety, but may also be associated with their ability to uncouple mitochondria. The increase in membrane permeability may prevent hyperpolarization caused by amiodarone and thus prevent formation of reactive oxygen species.

To assess the contribution of protonophore properties of the SkQ derivatives, the protective effect of SkQ3 was compared with the effects of tetraphenylphosphonium (TPP) and dodecyl tetraphenylphosphonium (C12-TPP), which do not contain quinone moiety (which determines the direct antioxidant effect), but are also able to penetrate into mitochondria and cause their uncoupling.

Figure 8:
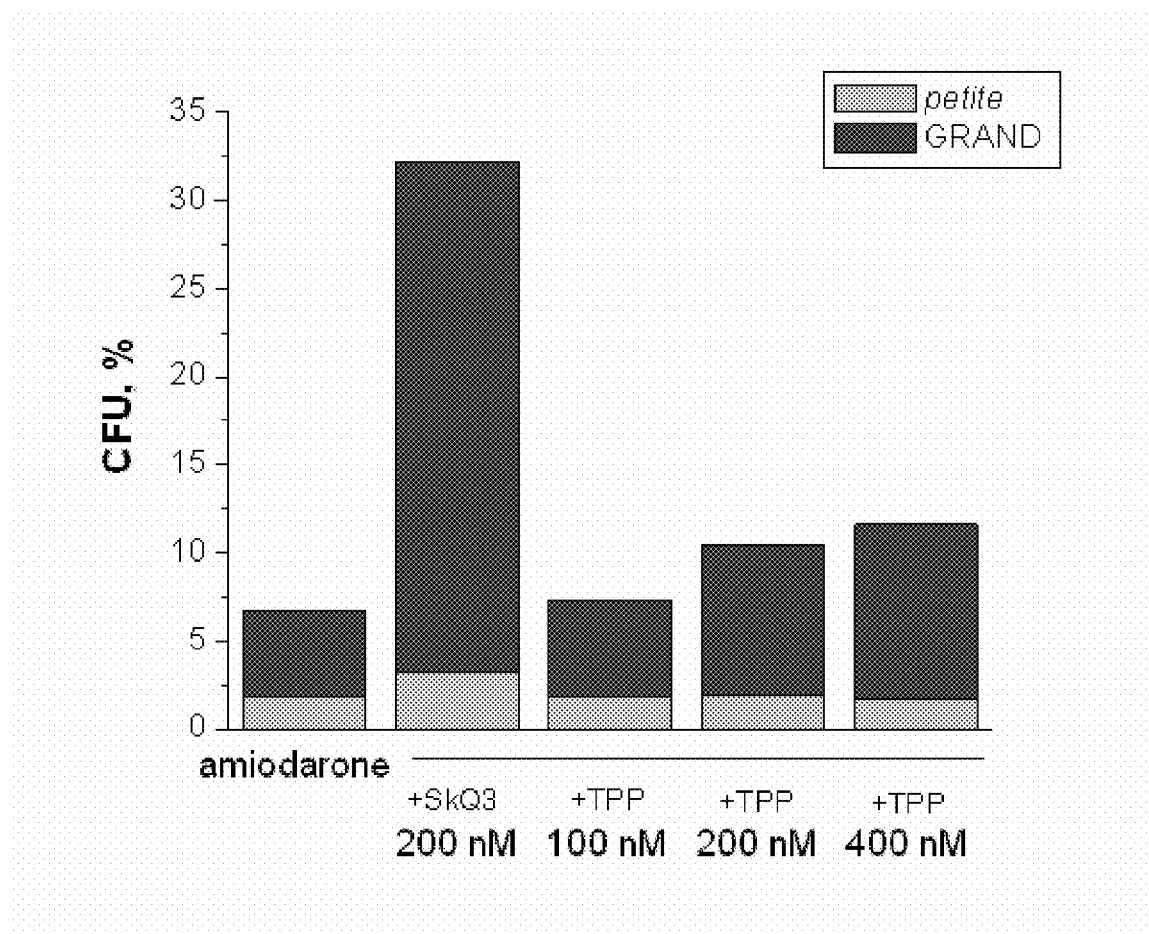
FIG. 8 is a graphic representation of yeast cells exposed to amiodarone (80 µM), where survival of petite forms unable to grow on non-fermented substrate was separately which shows the comparison of the protective effect of SkQ3 and tetraphenylphosphonium (TPP).
Figure 9:
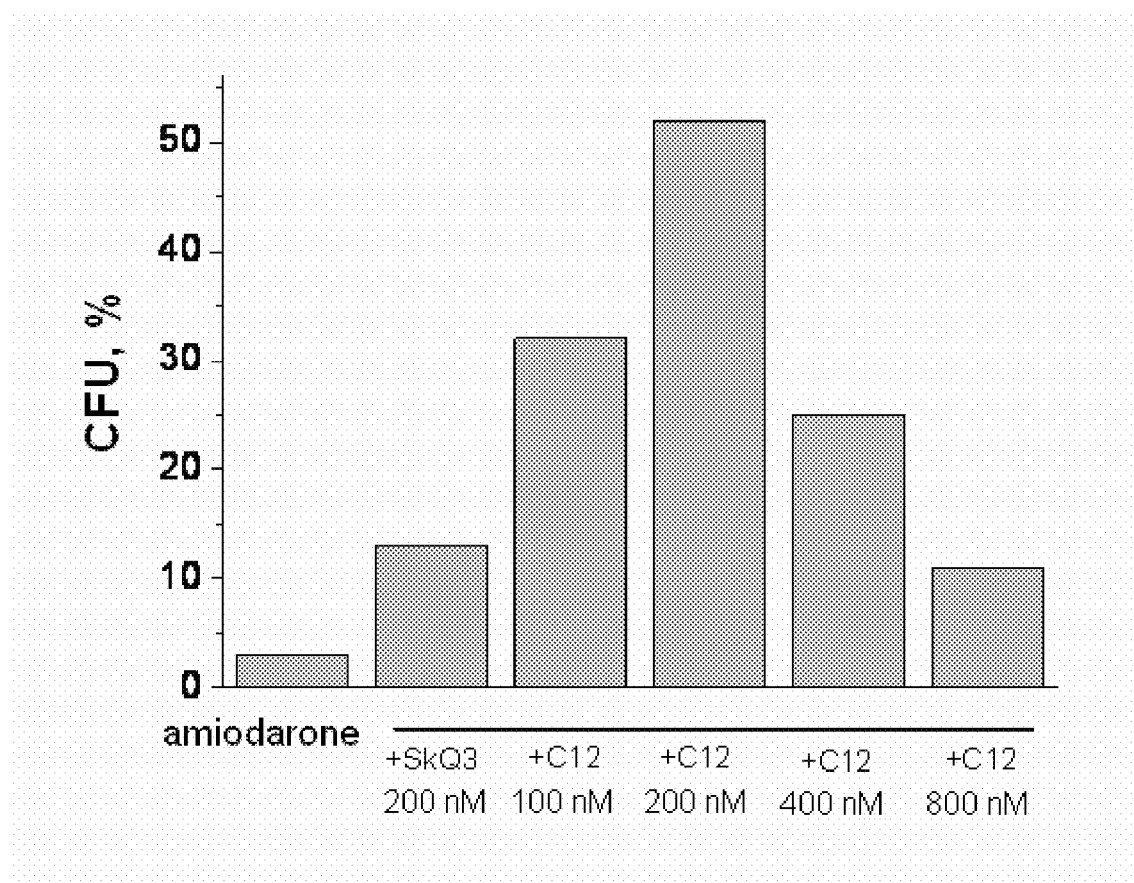
FIG. 9 is a graphic representation of yeast cells exposed to amiodarone (80 µM) CFU which shows the comparison of the protective effect of SkQ3 and dodecyl tetraphenylphosphonium (C12).

The results show that TPP does not have a significant effect in the concentration range from 100 nM to 400 nM (FIG. 8), whereas dodecyl tetraphenylphosphonium appeared to be even more effective than the tested antioxidants (FIG. 9). In the case of C12-TPP, there was a pronounced concentration dependence of the effect similar to that described for FCCP and SF in the literature (Pozniakowsky et al. (2005) *J. Cell Biol.* 168:257-269) with an optimum concentration of 200 nM.

Example 5

Pharmaceutical Compositions

The following is a representation of pharmaceutical compositions according to the disclosure for oral administration.
Pharmaceutical Composition 1—Gelatin Capsules:

| Ingredient | Amount (mg/capsule) |
| --- | --- |
| Compound of structure (I) | 0.0015-1000 |
| Starch | 0-650 |
| Starch powder | 0-650 |
| Liquid silicone | 0-15 |

Pharmaceutical Composition 2—Tablets:

| Ingredient | Amount (mg/capsule) |
| --- | --- |
| Compound of structure (I) | 0.0015-1000 |
| Microcrystalline cellulose | 200-650 |
| Silicon dioxide powder | 10-650 |
| Stearic acid | 5-15 |

Pharmaceutical Composition 3—Tablets:

| Ingredient | Amount (mg/capsule) |
|---|---|
| Compound of structure (I) | 0.0015-1000 |
| Starch | 45 |
| Microcrystalline cellulose | 35 |
| Polyvinylpyrrolidone (10% aqueous solution) | 4 |
| Carboxymethylcellulose, sodium salt | 4.5 |
| Talc | 1 |
| Magnesium stearate | 0.5 |

Pharmaceutical Composition 4—Suspensions:

| Ingredient | Amount (mg/5 ml) |
|---|---|
| Compound of structure (I) | 0.0015-1000 |
| Syrup | 1.25 |
| Benzoic acid solution | 0.10 |
| Carboxymethylcellulose, sodium salt | 50 |
| Flavoring | By necessity |
| Coloring | By necessity |
| Distilled water | Up to 5 ml |

The following is a representative soluble pharmaceutical composition for intraperitoneal, intra-arterial, and intravenous administration.

| Ingredient | Amount |
|---|---|
| Compound of structure (I) | 5 mg |
| Isotonic solution | 1000 ml |
| pH | 6.5 |

The following is a representative pharmaceutical composition for administration in aerosol form.

| Ingredient | Amount (weight percent) |
|---|---|
| Compound of structure (I) | 0.0025 |
| Ethanol | 25.75 |
| Difluorochloromethane | 70 |

The following is a representative pharmaceutical composition for administration in suppository form.

| Ingredient | Amount (mg/suppository) |
|---|---|
| Compound of structure (I) | 1 |
| Glycerides of saturated fatty acids | 2000 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of increasing proton permeability of a mitochondrial membrane in a cell, comprising contacting the cell with a compound of structure (1)

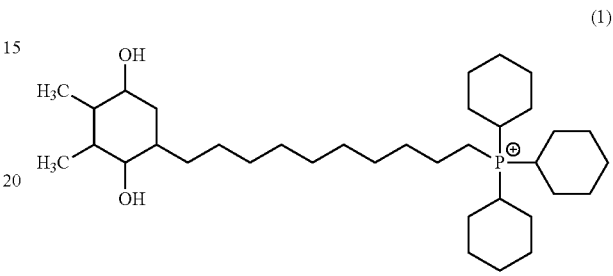

SkQ1 and its oxidized form.

2. A method of increasing proton permeability of a mitochondrial membrane in a cell, comprising contacting the cell with a compound of structure (2)

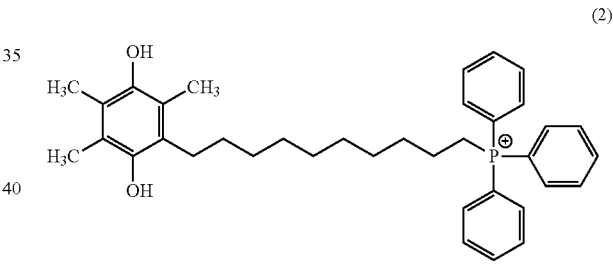

SkQ3 and its oxidized form.

3. A method of increasing proton permeability of a mitochondrial membrane in a cell, comprising contacting the cell with a compound of structure (3)

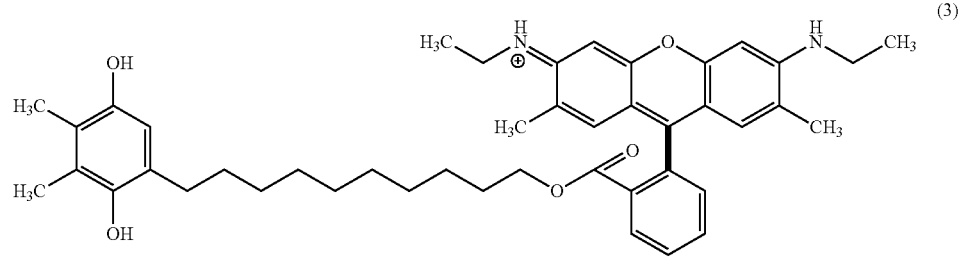

SkQR1 and its oxidized form.

4. A method of increasing proton permeability of a mitochondrial membrane in a cell, comprising contacting the cell with a compound of structure (4)
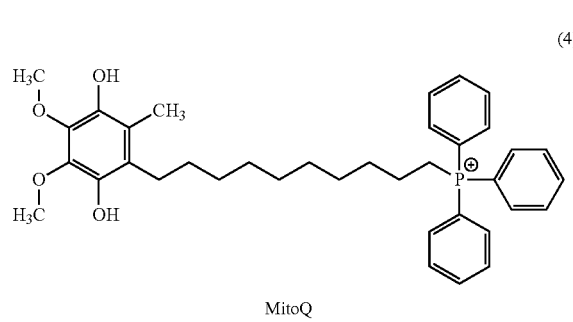 [SMILES: COc1c(O)c(C)c(CCCCCCCCCC[P+](c2ccccc2)(c2ccccc2)c2ccccc2)c(O)c1OC]
MitoQ
and its oxidized form.
5. A method of increasing proton permeability of a mitochondrial membrane in a cell, comprising contacting the cell with a compound of structure (5)
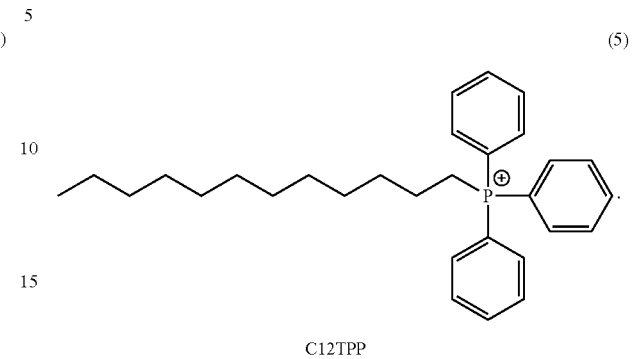
C12TPP
* * * * *